US012735487B2

(12) United States Patent
Zhu et al.

(10) Patent No.: US 12,735,487 B2
(45) **Date of Patent: *Sep. 15, 2026**

(54) MULTI-SPECIFIC ANTIBODIES AND METHODS OF MAKING AND USING THEREOF

(71) Applicants: SYSTIMMUNE, INC., Redmond, WA (US); SICHUAN BAILI PHARMACEUTICAL CO. LTD., Chengdu (CN)

(72) Inventors: Yi Zhu, Chengdu (CN); Ole Olsen, Everett, WA (US); Dong Xia, Redmond, WA (US); David Jellyman, Duvall, WA (US); Katrina Bykova, Seattle, WA (US); Anne-Marie Rousseau, Seattle, WA (US); Bill Brady, Bothell, WA (US); Blair Renshaw, Renton, WA (US); Brian Kovacevich, Snohomish, WA (US); Yu Liang, Redmond, WA (US); Zeren Gao, Redmond, WA (US)

(73) Assignee: SYSTIMMUNE, INC., Redmond, WA (US)

( * ) Notice: Subject to any disclaimer, the term of this patent is extended or adjusted under 35 U.S.C. 154(b) by 469 days.

This patent is subject to a terminal disclaimer.

(21) Appl. No.: 16/615,123

(22) PCT Filed: Jun. 22, 2018

(86) PCT No.: PCT/US2018/039157

§ 371 (c)(1),
(2) Date: Nov. 19, 2019

(87) PCT Pub. No.: WO2019/005640

PCT Pub. Date: Jan. 3, 2019

(65) Prior Publication Data

US 2020/0157224 A1 May 21, 2020

Related U.S. Application Data

(60) Provisional application No. 62/524,558, filed on Jun. 25, 2017.

(51) Int. Cl.

| | |
|---|---|
| ***C07K 16/28*** | (2006.01) |
| ***A61K 35/16*** | (2015.01) |
| ***C07K 16/32*** | (2006.01) |
| *A61K 45/06* | (2006.01) |

(52) U.S. Cl.

CPC .......... *C07K 16/2827* (2013.01); *A61K 35/16* (2013.01); *C07K 16/2809* (2013.01); *C07K 16/2878* (2013.01); *C07K 16/32* (2013.01); *A61K 45/06* (2013.01); *C07K 2317/31* (2013.01); *C07K 2317/622* (2013.01); *C07K 2317/64* (2013.01); *C07K 2317/66* (2013.01); *C07K 2317/73* (2013.01)

(58) Field of Classification Search
None
See application file for complete search history.

(56) References Cited

U.S. PATENT DOCUMENTS

| | | | | |
|---|---|---|---|---|
| 11,787,863 | B2 * | 10/2023 | Zhu .................... | C07K 16/2803 424/135.1 |
| 12,029,761 | B2 * | 7/2024 | Zhu .................... | C07K 14/7051 |
| 2009/0297513 | A1 | 12/2009 | Garcia-Martinez et al. | |
| 2015/0259414 | A1 | 9/2015 | Feldhaus et al. | |
| 2015/0346208 | A1 * | 12/2015 | Couto ................ | C07K 16/2896 530/387.9 |
| 2016/0130326 | A1 | 5/2016 | Meyer et al. | |
| 2017/0029529 | A1 | 2/2017 | Croasdale et al. | |
| 2021/0024630 | A1 * | 1/2021 | Zhu .................... | C07K 16/2809 |
| 2022/0002406 | A1 * | 1/2022 | Zhu .................... | C07K 16/2809 |

FOREIGN PATENT DOCUMENTS

| | | | | |
|---|---|---|---|---|
| WO | WO-2008119567 | A2 * | 10/2008 | ........... A61K 39/395 |
| WO | WO 2009/155724 | A | 12/2009 | |
| WO | WO-2017011342 | A1 * | 1/2017 | ........... C07K 16/468 |
| WO | WO-2017064221 | A1 * | 4/2017 | ............. C07K 16/08 |

OTHER PUBLICATIONS

Michaelson et alpha, mAbs 1:2, 128-141; Mar./Apr. 2009. (Year: 2009).*

Hu et al., Four-in-one antibodies have superior cancer inhibitory activity against EGFR, HER2, HER3, and VEGF through disruption of HER/MET crosstalk. Cancer Res. Jan. 1, 2015;75(1):159-70. especially p. 161 Fig. 1.

Clin Cancer Res. Dec. 1, 2016;22(23):5829-5838. Epub May 17, 2016. Characterization of CD33/CD3 Tetravalent Bispecific Tandem Diabodies (TandAbs) for the Treatment of Acute Myeloid Leukemia. especially abstract.

* cited by examiner

*Primary Examiner* — Gary B Nickol
*Assistant Examiner* — Cheom-Gil Cheong
(74) *Attorney, Agent, or Firm* — EpiMED LLC

(57) ABSTRACT

The disclosure provides a tetra-specific antibody monomer having a N-terminal and a C-terminal, comprising in tandem from the N-terminal to the C-terminal, a first scFv domain at the N-terminal, a second scFv domain, a Fab domain, a Fc domain, and a third scFv at the C-terminal, wherein the first scFv domain, the second scFv domain, the Fab domain, and the third scFv domain each has a binding specificity against a different antigen. In one embodiment, the antigen is a tumor antigen, an immune signaling antigen, or a combination thereof. In one embodiment, the antigen includes CD19, CD3, CD137, 4-1BB, and PD-L1. Multi-specific antibodies comprising the disclosed tetra-specific antibodies are also provided.

7 Claims, 8 Drawing Sheets

Specification includes a Sequence Listing.

| Antibody ID | Domain 1 | Domain 2 | Domain 3 | Fc | Domain 4 |
|---|---|---|---|---|---|
| | LH-scFv | LH-scFv | Fab | | HL-scFv |
| SI-38E34 | 21D4 | 284A10 | 420H5 | n2 | PL221 |
| SI-38E35 | 21D4 | 284A10 | 466F6 | n2 | PL221 |
| SI-38E36 | 21D4 | 284A10 | 460C3 | n2 | PL221 |
| SI-38X19 | 21D4 | 284A10* | - | - | - |
| | HD37 | I2C* | - | - | - |

FIG. 7

| Antibody ID | Domain 1 | Humanized Variant | Domain 2 | Humanized Variant | Domain 3 | Humanized Variant | IgG Fc | Domain 4 | Humanized Variant |
|---|---|---|---|---|---|---|---|---|---|
| | LH-scFv | | LH-scFv | | Fab | | | HL-scFv | |
| SI-38E34 | 21D4 | na | 284A10 | H1L1 | 420H5 | H3L3 | n2 | PL221 | H1L1 |
| SI-38E35 | 21D4 | na | 284A10 | H1L1 | 466F6 | H2L5 | n2 | PL221 | H1L1 |
| SI-38E36 | 21D4 | na | 284A10 | H1L1 | 460C3 | H1L1 | n2 | PL221 | H1L1 |
| SI-38X19 | 21D4 | na | 284A10* | H1L1 | - | - | - | - | - |
| | HD37 | | I2C* | - | - | - | - | - | - |

FIG. 8

MULTI-SPECIFIC ANTIBODIES AND METHODS OF MAKING AND USING THEREOF

CROSS REFERENCE TO RELATED APPLICATION

This application claims the benefit of U.S. Provisional Patent Application No. 62/524,558, filed Jun. 25, 2017, which application is expressly incorporated herein by reference in its entirety.

SEQUENCE LISTING

The content of the ASCII text file of the sequence listing named "036_ST25", which is 51,934 bytes in size was created on and electronically submitted via EFS-Web Apr. 11, 2022, is incorporated herein by reference in its entirety.

TECHNICAL FIELD

The present disclosure generally relates to the technical field of biologic therapeutics, and more particularly relates to making and using multi-specific antibodies.

BACKGROUND

Cancer cells develop various strategies to evade the immune system. One of the underlaying mechanisms for the immune escape is the reduced recognition of cancer cells by the immune system. Defective presentation of cancer specific antigens or lack of thereof results in immune tolerance and cancer progression. In the presence of effective immune recognition tumors use other mechanisms to avoid elimination by the immune system. Immunocompetent tumors create suppressive microenvironment to downregulate the immune response. Multiple players are involved in shaping the suppressive tumor microenvironment, including tumor cells, regulatory T cells, Myeloid-Derived Suppressor cells, stromal cells, and other cell types. The suppression of immune response can be executed in a cell contact-dependent format as well as in and a contact-independent manner, via secretion of immunosuppressive cytokines or elimination of essential survival factors from the local environment. Cell contact-dependent suppression relies on molecules expressed on the cell surface, e.g. Programmed Death Ligand 1 (PD-L1), T-lymphocyte-associated protein 4 (CTLA-4) and others [Dunn, et al., 2004, Immunity, 21 (2): 137-48; Adachi & Tamada, 2015, Cancer Sci., 106 (8): 945-50].

As the mechanisms by which tumors evade recognition by the immune system continue to be better understood new treatment modalities that target these mechanisms have recently emerged. On Mar. 25, 2011, the U. S. Food and Drug Administration (FDA) approved ipilimumab injection (Yervoy, Bristol-Myers Squibb) for the treatment of unresectable or metastatic melanoma. Yervoy binds to cytotoxic T-lymphocyte-associated protein 4 (CTLA-4) expressed on activated T cells and blocks the interaction of CTLA-4 with CD80/86 on antigen-presenting cells thereby blocking the negative or inhibitory signal delivered into the T cell through CTLA-4 resulting in re-activation of the antigen-specific T cell leading to, in many patients, eradication of the tumor. A few years later in 2014 the FDA approved Keytruda (Pembrolizumab, Merck) and Opdivo (Nivolumab, Bristol-Myers Squibb) for treatment of advanced melanoma. These monoclonal antibodies bind to PD-1 which is expressed on activated and/or exhausted T cells and block the interaction of PD-1 with PD-L1 expressed on tumors thereby eliminating the inhibitory signal through PD-1 into the T cell resulting in re-activation of the antigen-specific T cell leading to again, in many patients, eradication of the tumor. Since then additional clinical trials have been performed comparing the single monoclonal antibody Yervoy to the combination of the monoclonal antibodies Yervoy and Opdivo in the treatment of advanced melanoma which showed improvement in overall survival and progression-free survival in the patients treated with the combination of antibodies. (Hodi et al., 2016, Lancet Oncol. 17 (11): 1558-1568, Hellman et al., 2018, Cancer Cell 33 (5): 853-861). However, as many clinical trials have shown a great benefit of treating cancer patients with monoclonal antibodies that are specific for one or more immune checkpoint molecules data has emerged that only those patients with a high mutational burden that generates a novel T cell epitope(s) which is recognized by antigen-specific T cells show a clinical response (Snyder et al., 2014, NEJM 371:2189-2199). Those patients that have a low tumor mutational load mostly do not show an objective clinical response (Snyder et al., 2014, NEJM 371:2189-2199, Hellman et al., 2018, Cancer Cell 33 (5): 853-861).

In recent years other groups have developed an alternate approach that does not require the presence of neoepitope presentation by antigen-presenting cells to activate T cells. One example is the development of a bi-specific antibody where the binding domain of an antibody which is specific for a tumor associated antigen, e.g., CD19, is linked to and antibody binding domain specific for CD3 on T cells thus creating a bi-specific T cell engager or BiTe molecule. In 2014, the FDA approved a bi-specific antibody called Blinatumumab for the treatment of Precursor B-Cell Acute Lymphoblastic Leukemia. Blinatumumab links the scFv specific for CD19 expressed on leukemic cells with the scFv specific for CD3 expressed on T cells (Bejnjamin and Stein 2016, Ther Adv Hematol 7 (3): 142-146). However, despite an initial response rate of >50% in patients with relapsed or refractory ALL many patients are resistant to Blinatumumab therapy or relapse after successful treatment with Blinatumumab. Evidence is emerging that the resistant to Blinatumumab or who relapse after Blinatumumab treatment is attributable to the expression of immune checkpoint inhibitory molecules expressed on tumor cells such as PD-L1 that drives an inhibitory signal through PD-1 expressed on activated T cells (Feucht et al., 2016, Oncotarget 7 (47): 76902-76919). In a case study of a patient who was resistant to therapy with Blinatumumab a second round of Blinatumumab therapy was performed but with the addition of a monoclonal antibody, pembrolizumab (Keytruda, Merck), which specific for PD-1 and blocks the interaction of T cell-expressed PD-1 with tumor cell expressed PD-L1 resulted in a dramatic response and reduction of tumor cells in the bone marrow from 45% to less than 5% in this one patient (Feucht et al., 2016, Oncotarget 7 (47): 76902-76919). These results show that combining a bi-specific BiTe molecule with one or more monoclonal antibodies can significantly increase clinical activity compared to either agent alone.

SUMMARY

The present disclosure provides, among others, tetra-specific antibody monomers, antibodies containing tetra-specific monomers, antigen-binding fragments thereof, multi-specific antibodies, immuno-conjugates comprising the disclosed antibodies or monomers, methods of making disclosed monomers, antigen-binding fragments, and antibodies, and methods of using the disclosed molecules for treating cancer.

In one aspect, the application provides tetra-specific antibody monomers. In one embodiment, the tetra-specific antibody monomer has a N-terminal and a C-terminal and include in tandem from the N-terminal to the C-terminal, a first scFv domain at the N-terminal, a second scFv domain, a Fab domain, a Fc domain, and a third scFv at the C-terminal. The first scFv domain, the Fab domain, the second scFv domain, and the third scFv domain each has a binding specificity against a different antigen.

In one embodiment, the antigen includes a tumor antigen, an immune signaling antigen, or a combination thereof. In one embodiment, the first scFv domain, the Fab domain, the second scFv domain, and the third scFv domain each has a binding specificity against a tumor antigen or an immune signaling antigen. In one embodiment, the first scFv domain has a binding specificity against a tumor antigen. In one embodiment, the first scFv domain has a binding specificity against an immune signaling antigen. In one embodiment, the second scFv domain has a binding specificity against a tumor antigen. In one embodiment, the second scFv domain has a binding specificity against an immune signaling antigen. In one embodiment, the Fab domain has a binding specificity against a tumor antigen. In one embodiment, the Fab domain has a binding specificity against an immune signaling antigen. In one embodiment, the third scFv domain has a binding specificity against a tumor antigen. In one embodiment, the third scFv domain has a binding specificity against a tumor antigen.

In one embodiment, the tetra-specific monomer includes the first scFv domain, the second scFv domain, the Fab domain, and the third scFv domain, each independently has a binding specificity against an antigen selected from CD19, CD3, CD137, 4-1BB, PD-L1, ROR1, CD28, 41BB, CEA, HER2, EGFRvIII, EGFR, LMP1, LMP2A, Mesothelin, PSMA, EpCAM, glypimay-3, gpA33, GD2, TROP2, NKG2D, BCMA, CD20, CD33, CD123, CD22, CD30, PD1, OX40, GITR, TIGIT, TIM-3, LAG-3, CTLA4, CD40, VISTA, ICOS, BTLA, LIGHT, HVEM, CSF1R, CD73, and CD39. In one embodiment, the scFv domain, the second scFv domain, the Fab domain, and the third scFv domain each independently has a binding specificity against tumor specific antigens including, but not limited to, CD19, CD3, CD137, ROR1, CEA, HER2, EGFR, EGFRVIII, LMP1, LMP2A, Mesothelin, PSMA, EpCAM, glypimay-3, gpA33, GD2, TROP2, BCMA, CD20, CD33, CD123, CD22, CD30, or immune checkpoint modulators including, without limitation, PD-L1, PD1, OX40, 4-1BB, GITR, TIGIT, TIM-3, LAG-3, CTLA4, CD40, VISTA, ICOS, BTLA, Light, HVEM, CD73, CD39, etc. In one embodiment, one set of scFv domain may specifically bind to an immune checkpoint modulators or a tumor antigen. The scFv specific to CD3 component may be on either C or N terminal of heave or light chains.

In one embodiment, the first scFv domain, the second scFv domain, the Fab domain, and the third scFv domain each independently has a binding specificity against an antigen selected from CD19, CD3, CD137M, PD-L1, and 4-1BB. In one embodiment, the first scFv domain has a binding specificity against CD19. In one embodiment, the second scFv domain has a binding specificity against CD3. In one embodiment, the Fab domain has a binding specificity against 4-1BB or CD137. In one embodiment, the third scFv domain has a binding specificity against PD-L1.

In one embodiment, the first scFv domain has a binding specificity against CD19,, the second scFv domain has a binding specificity against CD3, the Fab domain has a binding specificity against 4-1BB, and the third scFv domain has a binding specificity against PD-L1. In one embodiment, the first scFv domain has a binding specificity against CD19,, the second scFv domain has a binding specificity against CD3, the Fab domain has a binding specificity against CD137, and the third scFv domain has a binding specificity against PD-L1.

The scFv domain may include a linker linking the scFv domain to the heavy chain or light chain of the antibody. In one embodiment, the linker may include more than 10 amino acids. In one embodiment, the linker may include more than 15 amino acids long. In one embodiment, the linker may include less than 20 amino acids.

In one embodiment, the linker may comprises a gly-gly-gly-gly-ser (G4S) n linker (SEQ ID NO.41), and n may be an integral between 1 to 20. For example, n may be 2, 4, or 6. In one embodiment, the first scFv domain, the second scFv domain, or the third scFv domain may comprise a gly-gly-gly-gly-ser (G4S) n linker (SEQ ID NO.41), wherein n is 2 or 4.

Fc domain may be humanized. In one embodiment, the Fc domain is a human IgG1 Fc.

In one embodiment, the application provides a tetra-specific antibody monomers having an amino acid sequence having a percentage homology to SEQ ID NO. 38 and 39. The percentage homology is not less than 70%, 80%, 90%, 95%, 98% or 99%.

The application further provides antigen-binding fragments. In one embodiment, the application provides scFv domains. In one embodiment, the scFv domain has an amino acid sequence having a percentage homology to SEQ ID No. 2, 4, 6, 8, 10, 12, 26, 28, 30, 32, wherein the percentage homology is not less than 70%, 80%, 90%, 95%, 98% or 99%. In one embodiment, the application provides Fab domains. In one embodiment, the Fab domain includes an amino acid sequence having a percentage homology to SEQ ID NO. 1-12,26-32, wherein the percentage homology is not less than 70%, 80%, 90%, 95%, 98% or 99%. The antigen-binding fragments disclosed herein may be used to construct the tetra-specific antibody monomers or multi-specific antibodies.

In one aspect, the application provides multi-specific antibodies. In one embodiment, the multi-specific antibody includes tetra-specific antibody monomers. In one embodiment, the multi-specific antibody includes two tetra-specific antibody monomers disclosed herein. As each tetra-specific antibody monomer has four antigen-binding domains, the multi-specific antibody disclosed may include 8 antigen-binding domains. In one embodiment, the antigen binding domains in such multi-specific antibody each independently has a binding specificity against a different antigen therefor providing an octa-specific antibody. In one embodiment, the multi-specific antibody is a penta-specific antibody. In one embodiment, the multi-specific antibody is a penta-specific antibody. In one embodiment, the multi-specific antibody is a penta-specific antibody a hexa-specific antibody. In one embodiment, the multi-specific antibody is a penta-specific antibody a hepta-specific antibody.

In one embodiment, the multi-specific antibody includes a dimer of a tetra-specific antibody monomer therefor providing a tetra-specific antibody. In one embodiment, the application provides an isolated, purified, or non-natural existing multi-specific antibodies. In one embodiment, the application provides a tetra-specific antibody having an amino acid sequence having a percentage homology to SEQ ID No. 37-40. The percentage homology is not less than 70%, 80%, 90%, 95%, 98% or 99%.

The application further provides isolated nucleic acid sequence encoding the tetra-specific antibody monomers, the multi-specific antibodies, or the antigen-binding fragments thereof. In one embodiment, the nucleic acid encodes an amino acid sequence having a percentage homology to the tetra-specific antibody monomer having a SEQ ID No. 37, 38. The percentage homology is not less than 70%, 80%, 90%, 95%, 98% or 99%.

The application further provides expression vectors and host cells comprising the nucleic acid sequences disclosed herein. In one embodiment, the host cell includes the expression vector. The host cell may be a prokaryotic cell or a eukaryotic cell.

The application further provides immuno-conjugates. In one embodiment, the immuno-conjugate includes a cytotoxic agent or an imaging agent linked to the multi-specific antibody disclosed herein through a linker.

The linker may be cleavable or non-cleavable. In one embodiment, the linker may include a covalent bond such as an ester bond, an ether bond, an amid bond, a disulphide bond, an imide bond, a sulfone bond, a phosphate bond, a phosphorus ester bond, a peptide bond, or a combination thereof. In one embodiment, the linker comprises a hydrophobic poly(ethylene glycol) linker.

The cytotoxic agent may include a chemotherapeutic agent, a growth inhibitory agent, a cytotoxic agent from class of calicheamicin, an antimitotic agent, a toxin, a radioactive isotope, a therapeutic agent, or a combination thereof. In one embodiment, the cytotoxic agent comprises a calicheamicin, ozogamicin, monomethyl auristatin E, emtansine, a derivative or a combination thereof.

The imaging agent may be any compound useful for imaging purpose. In one embodiment, the imaging agent may be radionuclide, a florescent agent, a quantum dots, or a combination thereof.

The application further provides pharmaceutical composition. In one embodiment, the pharmaceutical composition comprises a pharmaceutically acceptable carrier and the tetra-specific antibody monomer disclosed herein. In one embodiment, the pharmaceutical composition comprises a pharmaceutically acceptable carrier and the multi-specific antibody disclosed herein. In one embodiment, the pharmaceutical composition comprises a pharmaceutically acceptable carrier and the antigen-binding fragment disclosed herein. In one embodiment, the pharmaceutical composition comprises a pharmaceutically acceptable carrier and the immuno-conjugate disclosed herein.

In one embodiment, the pharmaceutical composition further includes a therapeutic agent. Example therapeutic agents include without limitation a radioisotope, radionuclide, a toxin, a chemotherapeutic agent, an antibody, an enzyme, or a combination thereof. In one embodiment, the therapeutic agent comprises an anti-estrogen agent, a receptor tyrosine kinase inhibitor, a kinase inhibitor, a cell cycle inhibitor, a DNA, RNA or protein synthesis inhibitor, a RAS inhibitor, or a combination thereof.

In one embodiment, the therapeutic agent comprises a check point inhibitor. In one embodiment, the therapeutic agent comprises an inhibitor of PD1, PDL1, CTLA4, 4-1BB, OX40, GITR, ICOS, LIGHT, TIM3, LAG3, TIGIT, CD40, CD27, HVEM, BTLA, VISTA, B7H4, CSF1R, NKG2D, CD73, a derivative or a combination thereof.

In a further aspect, the application provides methods for making the tetra-specific antibody monomers, the multi-specific antibodies, the antigen-binding fragments thereof, and immuno-conjugates thereof. In one embodiment, the method includes the steps of culturing the host cell containing the nucleic acid sequences disclosed herein such that the DNA sequence encoding the antibody is expressed and purifying the antibody. In one embodiment, the antibody is a tetra-specific antibody.

In a further aspect, the application provides methods of using the tetra-specific antibody monomers, the multi-specific antibodies, the antigen-binding fragments thereof, and immuno-conjugates thereof for cancer treatment. In one embodiment, the method includes the step of administering tetra-specific antibody monomers, the multi-specific antibodies, the antigen-binding fragments thereof, and immuno-conjugates thereof, or pharmaceutical composition thereof to a subject in need of such treatment. In one embodiment, the method includes the step of administering to the subject an effective amount of the tetra-specific antibody.

In one embodiment, the method includes directly injecting into the tumour site an effective amount of multi-specific monomers, multi-specific antibodies, the immuno-conjugates, the antigen-binding fragment thereof.

Varieties of cancer may be prevented or treated. In one embodiment, the cancer may have cells expressing ROR1, CEA, HER2, EGFR, EGFR VIII, LMP1, LMP2A, Mesothelin, PSMA, EpCAM, glypimay-3, gpA33, GD2, TROP2, NKG2D, BCMA, PD-L1, 4-1BB, CD3, CD19, CD20, CD33, CD137, CD123, CD22, or CD30. Example cancers include without limitation breast cancer, colorectal cancer, anal cancer, pancreatic cancer, gallbladder cancer, bile duct cancer, head and neck cancer, nasopharyngeal cancer, skin cancer, melanoma, ovarian cancer, prostate cancer, urethral cancer, lung cancer, non-small lung cell cancer, small cell lung cancer, brain tumor, glioma, neuroblastoma, esophageal cancer,,, gastric cancer, liver cancer, kidney cancer, bladder cancer, cervical cancer, endometrial cancer, thyroid cancer, eye cancer, sarcoma, bone cancer, leukemia, myeloma or lymphoma.

In one embodiment, the method may further include co-administering an effective amount of a therapeutic agent. In one embodiment, the therapeutic agent may include an antibody, a chemotherapy agent, an enzyme, or a combination thereof. In one embodiment, the therapeutic agent may include an anti-estrogen agent, a receptor tyrosine kinase inhibitor, a kinase inhibitor, a cell cycle inhibitor, a DNA, RNA or protein synthesis inhibitor, a RAS inhibitor, or a combination thereof. In one embodiment, the therapeutic agent may include a check point inhibitor. In one embodiment, the therapeutic agent may include an inhibitor of PD1, PD-L1, cd19, cd3, cd137, CTLA4, 4-1BB, OX40, GITR, ICOS, LIGHT, TIM3, LAG3, TIGIT, CD40, CD27, HVEM, BTLA, VISTA, B7H4, CSF1R, NKG2D, CD73, a derivative or a combination thereof.

In one embodiment, the therapeutic agent may include capecitabine, cisplatin, Cyclophosphamide, methotrexate, 5-fluorouracil, Doxorubicin, cyclophosphamide, Mustine, vincristine, procarbazine, prednisolone, bleomycin, vinblastine, dacarbazine, etoposide, Epirubicin, pemetrexed, folinic acid, gemicitabine, oxaliplatin, irinotecan, topotecan, camptothecin, docetaxel, paclitaxel,, fulvestrant, tamoxifen, letrozole, exemestane, anastrozole, aminoglutethimide, testolactone, vorozole, formestane, fadrozole, erlotinib, lafatinib, dasatinib, gefitinib, osimertinib, vandertanib, afatinib, imatinib, pazopinib, lapatinib, sunitinib, nilotinib, sorafenib, nab-palitaxel, Everolimus, temsirolimus, Dabrafenib, vemurafenib, trametinib, vintafolide, apatinib, crizotinib, periforsine, olaparib, Bortezomib, tofacitinib, trastuzumab, a derivative or a combination thereof.

The subject may be a human. In one embodiment, the subject may be suffering from cancer. The application further provides solutions comprising an effective concentration of the multi-specific antibodies, monomers, or immunoconjugates disclosed herein. In one embodiment, the solution is blood plasma in a subject.

The objectives and advantages of the disclosure may become apparent from the following detailed description of example embodiments thereof in connection with the accompanying drawings. Still other embodiments may become readily apparent to those skilled in the art from the following detailed description, wherein are described embodiments by way of illustrating the best mode contemplated. As may be realized, other and different embodiments are possible and the embodiments' several details are capable of modifications in various obvious respects, all without departing from their spirit and the scope. Accordingly, the drawings and detailed description are to be regarded as illustrative in nature and not as restrictive.

BRIEF DESCRIPTION OF THE FIGURES

The foregoing and other features of this disclosure may become more fully apparent from the following description and appended claims, taken in conjunction with the accompanying tables and figures. Understanding that these tables and figures depict only several embodiments arranged in accordance with the disclosure and are, therefore, not to be considered limiting of its scope, the disclosure may be described with additional specificity and detail through use of the accompanying drawings, in which:

FIG. 7 shows example tetra-specific antibodies with CD19 tumor antigen recognition domain (Table 1).

FIG. 8 provides a list of example tetra-specific antibodies disclosed herein (Table 2).

DETAILED DESCRIPTION

Figure 1:
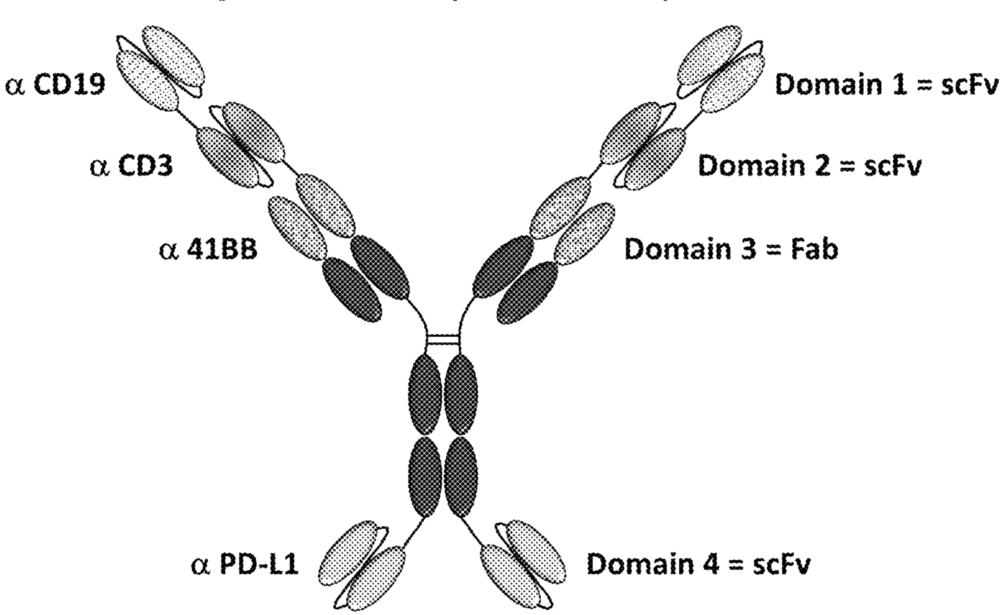
FIG. 1 is a diagram of the general format of a guided navigation control (GNC) tetra-specific antibody.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It may be readily understood that the aspects of the present disclosure, as generally described herein, and illustrated in the Figures, can be arranged, substituted, combined, separated, and designed in a wide variety of different configurations, all of which are explicitly contemplated herein.

The disclosure provides, among others, isolated antibodies, methods of making such antibodies, tetra-specific or multi-specific molecules, antibody-drug conjugates and/or immuno-conjugates composed from such antibodies or antigen binding fragments, pharmaceutical compositions containing the antibodies, tetra-specific or multi-specific molecules, antibody-drug conjugates and/or immunoconjugates, method of making thereof, and method of using the disclosed molecules or composition for treatment of cancer.

The term "antibody" is used in the broadest sense and specifically covers single monoclonal antibodies (including agonist and antagonist antibodies), antibody compositions with polyepitopic specificity, as well as antibody fragments (e.g., Fab, $F(ab')_2$, and Fv), so long as they exhibit the desired biological activity. In some embodiments, the antibody may be monoclonal, polyclonal, chimeric, single chain, bispecific or bi-effective, simianized, human and humanized antibodies as well as active fragments thereof. Examples of active fragments of molecules that bind to known antigens include Fab, $F(ab')_2$, scFv and Fv fragments, including the products of an Fab immunoglobulin expression library and epitope-binding fragments of any of the antibodies and fragments mentioned above. In some embodiments, antibody may include immunoglobulin molecules and immunologically active portions of immunoglobulin molecules, i.e. molecules that contain a binding site that immunospecifically bind an antigen. The immunoglobulin can be of any type (IgG, IgM, IgD, IgE, IgA and IgY) or class (IgG1, IgG2, IgG3, IgG4, IgA1 and IgA2) or subclasses of immunoglobulin molecule. In one embodiment, the antibody may be whole antibodies and any antigen-binding fragment derived from the whole antibodies. A typical antibody refers to heterotetrameric protein comprising typically of two heavy (H) chains and two light (L) chains. Each heavy chain is comprised of a heavy chain variable domain (abbreviated as VH) and a heavy chain constant domain. Each light chain is comprised of a light chain variable domain (abbreviated as VL) and a light chain constant domain. The VH and VL regions can be further subdivided into domains of hypervariable complementarity determining regions (CDR), and more conserved regions called framework regions (FR). Each variable domain (either VH or VL) is typically composed of three CDRs and four FRs, arranged in the following order: FR1, CDR1, FR2, CDR2, FR3, CDR3, FR4 from amino-terminus to carboxy-terminus. Within the variable regions of the light and heavy chains there are binding regions that interacts with the antigen.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present disclosure may be made by the hybridoma method first described by Kohler & Milstein, *Nature,* 256:495 (1975), or may be made by recombinant DNA methods (see, e.g., U.S. Pat. No. 4,816,567).

The monoclonal antibodies may include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., *Proc. Natl. Acad. Sci. USA,* 81:6851-6855 [1984]).

Monoclonal antibodies can be produced using various methods including mouse hybridoma or phage display (see Siegel. Transfus. Clin. Biol. 9:15-22 (2002) for a review) or from molecular cloning of antibodies directly from primary B cells (see Tiller. New Biotechnol. 28:453-7 (2011)). In the present disclosure antibodies were created by the immunization of rabbits with both human PD-L1 protein and cells transiently expressing human PD-L1 on the cell surface. Rabbits are known to create antibodies of high affinity, diversity and specificity (Weber et al. Exp. Mol. Med. 49:e305). B cells from immunized animals were cultured in vitro and screened for the production of anti-PD-L1 antibodies. The antibody variable genes were isolated using recombinant DNA techniques and the resulting antibodies were expressed recombinantly and further screened for desired features such as ability to inhibit the binding of PD-L1 to PD-1, the ability to bind to non-human primate PD-L1 and the ability to enhance human T-cell activation. This general method of antibody discovery is similar to that described in Seeber et al. PLOS One. 9:e86184 (2014).

The term "antigen-or epitope-binding portion or fragment" refers to fragments of an antibody that are capable of binding to an antigen (PD-L1 in this case). These fragments may be capable of the antigen-binding function and additional functions of the intact antibody. Examples of binding fragments include, but are not limited to a single-chain Fv fragment (scFv) consisting of the VL and VH domains of a single arm of an antibody connected in a single polypeptide chain by a synthetic linker or a Fab fragment which is a monovalent fragment consisting of the VL, constant light (CL), VH and constant heavy 1 (CH1) domains. Antibody fragments can be even smaller sub-fragments and can consist of domains as small as a single CDR domain, in particular the CDR3 regions from either the VL and/or VH domains (for example see Beiboer et al., J. Mol. Biol. 296:833-49 (2000)). Antibody fragments are produced using conventional methods known to those skilled in the art. The antibody fragments are can be screened for utility using the same techniques employed with intact antibodies.

The "antigen-or epitope-binding fragments" can be derived from an antibody of the present disclosure by a number of art-known techniques. For example, purified monoclonal antibodies can be cleaved with an enzyme, such as pepsin, and subjected to HPLC gel filtration. The appropriate fraction containing Fab fragments can then be collected and concentrated by membrane filtration and the like. For further description of general techniques for the isolation of active fragments of antibodies, see for example, Khaw, B. A. et al. J. Nucl. Med. 23:1011-1019 (1982); Rousseaux et al. Methods Enzymology, 121:663-69, Academic Press, 1986.

Papain digestion of antibodies produces two identical antigen binding fragments, called "Fab" fragments, each with a single antigen binding site, and a residual "Fc" fragment, whose name reflects its ability to crystallize readily. Pepsin treatment yields an $F(ab')_2$ fragment that has two antigen combining sites and is still capable of cross-linking antigen.

The Fab fragment may contain the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other, chemical couplings of antibody fragments are also known.

"Fv" is the minimum antibody fragment which contains a complete antigen recognition and binding site. This region consists of a dimer of one heavy and one light chain variable domain in tight, non-covalent association. It is in this configuration that the three CDRs of each variable domain interact to define an antigen binding site on the surface of the VH-VL dimer. Collectively, the six CDRs confer antigen binding specificity to the antibody. However, even a single variable domain (or half of an Fv comprising only three CDRs specific for an antigen) has the ability to recognize and bind antigen, although at a lower affinity than the entire binding site.

The "light chains" of antibodies (immunoglobulins) from any vertebrate species can be assigned to one of two clearly distinct types, called kappa and lambda (A), based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. The heavy chain constant domains that correspond to the different classes of immunoglobulins are called a, delta, epsilon, v, and u, respectively. The subunit structures and three-dimensional configurations of different classes of immunoglobulins are well known.

A "humanized antibody" refers to a type of engineered antibody having its CDRs derived from a non-human donor immunoglobulin, the remaining immunoglobulin-derived parts of the molecule being derived from one (or more) human immunoglobulin(s). In addition, framework support residues may be altered to preserve binding affinity. Methods to obtain "humanized antibodies" are well known to those skilled in the art. (see, e.g., Queen et al., Proc. Natl Acad Sci USA, 86:10029-10032 (1989), Hodgson et al., Bio/Technology, 9:421 (1991)). In one embodiment, the "humanized antibody" may be obtained by genetic engineering approach that enables production of affinity-matured humanlike polyclonal antibodies in large animals such as, for example, rabbits (see, e.g. U.S. Pat. No. 7,129,084).

The terms "polypeptide", "peptide", and "protein", as used herein, are interchangeable and are defined to mean a biomolecule composed of amino acids linked by a peptide bond.

The terms "a", "an" and "the" as used herein are defined to mean "one or more" and include the plural unless the context is inappropriate.

By "isolated" is meant a biological molecule free from at least some of the components with which it naturally occurs. "Isolated," when used to describe the various polypeptides disclosed herein, means a polypeptide that has been identified and separated and/or recovered from a cell or cell culture from which it was expressed. Ordinarily, an isolated polypeptide may be prepared by at least one purification step. An "isolated antibody," refers to an antibody which is substantially free of other antibodies having different antigenic specificities.

"Recombinant" means the antibodies are generated using recombinant nucleic acid techniques in exogeneous host cells.

The term "antigen" refers to an entity or fragment thereof which can induce an immune response in an organism, particularly an animal, more particularly a mammal including a human. The term includes immunogens and regions thereof responsible for antigenicity or antigenic determinants.

Also as used herein, the term "immunogenic" refers to substances which elicit or enhance the production of antibodies, T-cells or other reactive immune cells directed against an immunogenic agent and contribute to an immune response in humans or animals. An immune response occurs when an individual produces sufficient antibodies, T-cells and other reactive immune cells against administered immunogenic compositions of the present disclosure to moderate or alleviate the disorder to be treated.

"Specific binding" or "specifically binds to" or is "specific for" a particular antigen or an epitope means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target.

Specific binding for a particular antigen or an epitope can be exhibited, for example, by an antibody having a KD for an antigen or epitope of at least about $10^{-4}$ M, at least about $10^{-5}$ M, at least about $10^{-6}$ M, at least about $10^{-7}$ M, at least about $10^{-8}$ M, at least about $10^{-9}$, alternatively at least about $10^{-10}$ M, at least about $10^{-11}$ M, at least about $10^{-12}$ M, or greater, where KD refers to a dissociation rate of a particular antibody-antigen interaction. In some embodiments, an antibody that specifically binds an antigen may have a KD that is 20-, 50-, 100-, 500-, 1000-, 5,000-, 10,000-or more times greater for a control molecule relative to the antigen or epitope.

Also, specific binding for a particular antigen or an epitope can be exhibited, for example, by an antibody having a KA or Ka for an antigen or epitope of at least 20-, 50-, 100-, 500-, 1000-, 5,000-, 10,000- or more times greater for the epitope relative to a control, where KA or Ka refers to an association rate of a particular antibody-antigen interaction.

"Homology" between two sequences is determined by sequence identity. If two sequences which are to be compared with each other differ in length, sequence identity preferably relates to the percentage of the nucleotide residues of the shorter sequence which are identical with the nucleotide residues of the longer sequence. Sequence identity can be determined conventionally with the use of computer programs. The deviations appearing in the comparison between a given sequence and the above-described sequences of the disclosure may be caused for instance by addition, deletion, substitution, insertion or recombination.

In one aspect, the application provides tetra-specific antibody monomers, antigen-binding fragments, and multi-specific antibodies. In one embodiment, the application provides tetra-specific antibodies.

In one embodiment, the disclosure provides tetra-specific antibodies with a binding specificity against four different antigen targets. In one embodiment, the antigen targets are tumor specific antigens, T cell receptor CD3 component, or immune checkpoint molecules. The tetra-specific antibodies may directly engage body's endogenous T cells to kill tumor cells independent of tumor antigen presentation by MHC to the antigen specific T cell receptors. In addition, the immune checkpoint modulating component of the tetra-specific antibodies may overcome the immunosuppressive tumor microenvironment to fully activate the exhausted T cells within the tumor microenvironment.

In one embodiment, the tetra-specific antibodies may have unique properties of directly engaging T cells at the same time modulating immune checkpoint or inhibiting Treg or other inhibitory immune cells or targeting tumor with component against tumor antigens. It will show benefit to the patients where BiTE or CAR-T treatment isn't appropriate. Particularly, the tetra-specific antibodies could demonstrate clinical benefit in solid tumor where BiTE-like technology or CAR-T treatment, which yet to show clinical benefit due to the limitations imposed by the inhibitory tumor microenvironment.

In one embodiment, the disclosure provides an engineered antibody with 4 different binding domains or a "tetra-specific antibody". One binding domain is specific for CD3 on T cells, a second binding domain is specific for a tumor associated antigen including but not limited to ROR1, CEA, HER2, EGFR, EGFRvIII, LMP1, LMP2A, Mesothelin, PSMA, EpCAM, glypican-3, gpA33, GD2, TROP2, BCMA, CD19, CD20, CD33, CD123, CD22, CD30, and a third and fourth binding domains are specific for two distinct immune checkpoint modulators such as PD-L1, PD-1, OX40, 4-1BB, GITR, TIGIT, TIM-3, LAG-3, CTLA4, CD40, VISTA, ICOS, BTLA, Light, HVEM, CD73, CD39, etc.

In one embodiment, the tetra-specific molecules (FIG. 1) target human CD19 SEQ ID NO. 25-32 a tumor associated antigen. In some embodiments, these targeted tetra-specific proteins carry an anti-human PD-L1 (SEQIDs 9-12), an anti-human 4-1BB (SEQIDs 13-24), an anti-human CD3 binding domain (SEQIDs 1-8). The tetra-specific molecule binding domains are arrayed such that the binding domain placement proceeds from the N-terminus to D1, scFv VLVH, followed by D2, scFv VLVH, D3 which is in the Fab position in this class of tetra-specific proteins, followed by the human IgG1 Fc and an scFv, VHVL, in D4.

In one embodiment, tetra-specific protein SI-38E34 (SEQIDs 37-40) is composed of an anti-human CD19 21D4 scFv, anti-human CD3 284A10 scFv, anti-human CD137 (Fab) and anti-human PD-L1 clone PL221G5 scFv occupying positions D1, D2, D3 and D4, respectively. D1, D2 and D3 are genetically linked through a 10 amino acid (G4S)×2 linker (SEQ ID NO.41), as is the C-terminus of the human IgG1 Fc and D4, resulting in a contiguous ~150 kDa heavy chain monomer peptide containing the binding specificities outlined above. All scFv molecules described herein contain a 20 amino acid flexible gly-gly-gly-gly-ser (G4S) X4 linker (SEQ ID NO.41) that operably links the VH and VL, regardless of the V-region orientation (LH or HL). The remaining position in the tetra-specific protein, Domain 3

(D3), consists of an IgG1 heavy chain, VH-CH1-Hinge-CH2-CH3, and its corresponding light chain, VL-CL, which can be either a kappa or lambda chain. D1 and D2 are genetically linked through a 10 amino acid (G4S)×2 linker (SEQ ID NO.41), as are D2, D3 and D4 resulting in a contiguous ~150 kDa heavy chain monomer peptide. When co-transfected with the appropriate light chain, the final symmetric tetra-specific peptide can be purified through the IgG1 Fc (Protein A/Protein G) and assayed to assess functional activity. Heavy and light chain gene "cassettes" were previously constructed such that V-regions could be easily cloned using either restriction enzyme sites (HindIII/NheI for the heavy chain and HindIII/BsiWI for the light chain) or "restriction-free cloning" such as Gibson Assembly (SGI-DNA, La Jolla, CA), Infusion (Takara Bio USA) or NEBuilder (NEB, Ipswich, MA), the latter of which was used here.

In one embodiment, tetra-specific proteins are produced through a process that involves design of the intact molecule, synthesis and cloning of the nucleotide sequences for each domain, expression in mammalian cells and purification of the final product. Nucleotide sequences were assembled using the Geneious 10.2.3 software package (Biomatters, Auckland, NZ) and broken up into their component domains for gene synthesis (Genewiz, South Plainsfield, NJ).

In one embodiment, SI-35E18 (SEQID 65 and 67) was split into its component domains where the anti-4-1BB scFv, VLVH, occupies D1, anti-human PD-L1 clone PL230C6 occupies D2 (Fab position), anti-human ROR1 Ig domain-specific clone 323H7 VHVL scFv occupies D3, and anti-human CD3 scFv, VHVL, occupies the C-terminal D4. Using NEBuilder web-based tools, 5' and 3' nucleotides were appended to each of the domains depending on their position in the larger protein so that each domain overlaps its flanking domains by 20-30 nucleotides which direct site-specific recombination, thus genetically fusing each domain in a single gene assembly step. Due to the high number of homologous regions in the tetra-specific nucleotide sequence, the N-terminal domains 1 and 2 are assembled separately from the C-terminal D3 and D4. The N- and C-terminal fragments were then assembled together in a second NEBuilder reaction. A small aliquot was transformed into *E. coli* DH10b (Invitrogen, Carlsbad, CA) and plated on TB+carbenicillin 100 μg/ml plates (Teknova, Hollister, CA) and incubated at 37C overnight. Resultant colonies were selected and 2 ml overnight cultures inoculated in TB+carbenicillin. DNA was prepared (Thermo-Fisher, Carlsbad, CA) from overnight cultures and subsequently sequenced (Genewiz, South Plainsfield, NJ) using sequencing primers (Sigma, St. Louis, MO) flanking each domain. All DNA sequences were assembled and analyzed in Geneious.

In another aspect, the application provides pharmaceutical compositions including the multi-specific antibody monomers, the multi-specific antibodies, the antigen-binding fragments, and the immuno-conjugates thereof, and methods of using the disclosed antibodies or pharmaceutical compositions for treatment of cancer.

The advantages of treating cancer using the disclosed multi-specific antibody monomers, the multi-specific antibodies, the antigen-binding fragments, the immuno-conjugates and composition thereof over currently existing therapies include, without limitation: 1) Inclusion of an IgG Fc domain will confer the characteristic of a longer half-life in serum compared to a bi-specific BiTe molecule; 2) Inclusion of two binding domains that are specific for immune checkpoint modulators, that can inhibit the suppressive pathways and engage the co-stimulatory pathways at the same time; and 3) Cross-link CD3 on T cells with tumor associated antigens thus "re-directing" T cells to kill the tumor without the need to remove T cells from the patient and genetically modify them to be specific for the tumor cell before re-introducing them back into the patient as done for chimeric antigen receptor T cells (CAR-T).

Formulation of the pharmaceutical composition may be accomplished according to standard methodology know to those of ordinary skill in the art.

In one embodiment, the antibodies and monomers according to the disclosure may be prepared in a physiologically acceptable formulation and may comprise a pharmaceutically acceptable carrier, diluent and/or excipient using known techniques. For example, the antibody according to the disclosure and as described herein including any functionally equivalent antibody or functional parts thereof, in particular, the monoclonal antibody including any functionally equivalent antibody or functional parts thereof is combined with a pharmaceutically acceptable carrier, diluent and/or excipient to form a therapeutic composition. Formulation of the pharmaceutical composition according to the disclosure may be accomplished according to standard methodology know to those of ordinary skill in the art.

With respect to the formulation of suitable compositions for administration to a subject such as a human patient in need of treatment, the antibodies disclosed herein may be mixed or combined with pharmaceutically acceptable carriers known in the art dependent upon the chosen route of administration. There are no particular limitations to the modes of application of the antibodies disclosed herein, and the choice of suitable administration routes and suitable compositions are known in the art without undue experimentation.

Suitable pharmaceutical carriers, diluents and/or excipients are well known in the art and include, for example, phosphate buffered saline solutions, water, emulsions such as oil/water emulsions.

"Pharmaceutically acceptable" refers to those compounds, materials, compositions, and dosage forms which are, within the scope of sound medical judgment, suitable for use contact with the tissues of human beings or animals without excessive toxicity, irritation, or other problem or complication, commensurate with a reasonable benefit/risk ratio.

In one embodiment, the pharmaceutical composition may include proteinaceous carriers such as, for example, serum albumin or immunoglobulin, particularly of human origin. Further biologically active agents may be present in the pharmaceutical composition of the disclosure dependent on the intended use. In one embodiment, the proteinaceous pharmaceutically active matter may be present in amounts between 1 ng and 10 mg per dose. Generally, the regime of administration should be in the range of between 0.1 μg and 10 mg of the antibody according to the disclosure, particularly in a range 1.0 μg to 1.0 mg, and more particularly in a range of between 1.0 μg and 100 μg, with all individual numbers falling within these ranges also being part of the disclosure. If the administration occurs through continuous infusion a more proper dosage may be in the range of between 0.01 μg and 10 mg units per kilogram of body weight per hour with all individual numbers falling within these ranges also being part of the disclosure.

The compositions of the present disclosure may be administered to a subject in the form of a solid, liquid or aerosol at a suitable, pharmaceutically effective dose. Examples of solid compositions include pills, creams, and implantable dosage units. Pills may be administered orally. Therapeutic creams may be administered topically. Implantable dosage units may be administered locally, for example, at a tumor site, or may be implanted for systematic release of the therapeutic composition, for example, subcutaneously. Examples of liquid compositions include formulations adapted for injection intramuscularly, subcutaneously, intravenously, intra-arterially, and formulations for topical and intraocular administration. Examples of aerosol formulations include inhaler formulations for administration to the lungs.

It is well known to those of ordinary skill in the art that the dosage of the composition may depend on various factors such as, for example, the condition of being treated, the particular composition used, and other clinical factors such as weight, size, sex and general health condition of the patient, body surface area, the particular compound or composition to be administered, other drugs being administered concurrently, and the route of administration.

The term "therapeutically effective amount" or "effective amount" refers to the amount of antibody which, when administered to a human or animal, elicits a response which is sufficient to result in a therapeutic effect in said human or animal, e.g., to ameliorate disease in a subject. The effective amount is readily determined by one of ordinary skill in the art following routine procedures. Where the disease is a cancer, the effective amount of the drug may inhibit (for example, slow to some extent, inhibit or stop) one or more of the following example characteristics including, without limitation, cancer cell growth, cancer cell proliferation, cancer cell motility, cancer cell infiltration into peripheral organs, tumor metastasis, and tumor growth. Wherein the disease is a mayer, the effective amount of the drug may alternatively do one or more of the following when administered to a subject: slow or stop tumor growth, reduce tumor size (for example, volume or mass), relieve to some extent one or more of the symptoms associated with the cancer, extend progression free survival, result in an objective response (including, for example, a partial response or a complete response), and increase overall survival time. To the extent the drug may prevent growth and/or kill existing cancer cells, it is cytostatic and/or cytotoxic.

A person skilled in the art have the ability to determine the effective amount or concentration of the antibodies disclosed therein to effective treat a condition such as a cancer. Other parameters such as the proportions of the various components in the pharmaceutical composition, administration does and frequency may be obtained by a person skilled in the art without undue experimentation. For example, a suitable solution for injection may contain, without limitation, from about 1 to about 20, from about 1 to about 10 mg antibodies per ml. The example dose may be, without limitation, from about 0.1 to about 20, from about 1 to about 5 mg/Kg body weight. The example administration frequency could be, without limitation, once per day or three times per week.

The compositions may be administered by standard routes of administration. In general, the composition may be administered by topical, oral, rectal, nasal, interdermal, intraperitoneal, or parenteral (for example, intravenous, subcutaneous, or intramuscular) routes. In addition, the composition may be incorporated into sustained release matrices such as biodegradable polymers, the polymers being implanted in the vicinity of where delivery is desired, for example, at the site of a tumor. The method includes administration of a single dose, administration of repeated doses at predetermined time intervals, and sustained administration for a predetermined period of time.

Although many forms of administration are possible, an example administration form would be a solution for injection, in particular for intravenous or intra-arterial injection. Usually, a suitable pharmaceutical composition for injection may include pharmaceutically suitable carriers or excipients such as, without limitation, a buffer, a surfactant, or a stabilizer agent. Example buffers may include, without limitation, acetate, phosphate or citrate buffer. Example surfactants may include, without limitation, polysorbate. Example stabilizer may include, without limitation, human albumin.

In one embodiment, the administration may be parenterally, e.g. intravenously. Preparations for parenteral administration include sterile aqueous or non-aqueous solutions, suspensions and emulsions. Non-aqueous solvents include without being limited to it, propylene glycol, polyethylene glycol, vegeTABLE oil such as olive oil, and injectable organic esters such as ethyl oleate. Aqueous solvents may be chosen from the group consisting of water, alcohol/aqueous solutions, emulsions or suspensions including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose) and others. Preservatives may also be present such as, for example, antimicrobials, anti-oxidants, chelating agents, inert gases, etc.

The antibody monomers, antibodies, antigen-binding fragments and immuno-conjugates thereof may be used in combination with a therapeutic agent or a composition comprising a therapeutic agent for treatment purpose.

In some embodiments, the multi-specific antibody molecule is used in combination with one or more additional therapeutic agents at an effective amount. The additional therapeutic agent includes an antibody, a chemotherapy agent, an enzyme, or a combination thereof. In some embodiment, the additional therapeutic agent may be an anti-estrogen agent, a receptor tyrosine kinase inhibitor, a kinase inhibitor, a cell cycle inhibitor, a DNA, RNA or protein synthesis inhibitor, a RAS inhibitor, or a combination thereof. In some embodiments, the additional therapeutic agent may be a check point inhibitor. In some embodiments, therapeutic agent comprises inhibitors of PD1, PDL1, CTLA4, 4-1BB, OX40, GITR, ICOS, LIGHT, TIM3, LAG3, TIGIT, CD40, CD27, HVEM, BTLA, VISTA, B7H4, CSF1R, NKG2D, CD73, a derivative or a combination thereof.

In one embodiment, the therapeutic agent may include capecitabine, cisplatin, trastuzumab, fulvestrant, tamoxifen, letrozole, exemestane, anastrozole, aminoglutethimide, testolactone, vorozole, formestane, fadrozole, letrozole, erlotinib, lafatinib, dasatinib, gefitinib, imatinib, pazopinib, lapatinib, sunitinib, nilotinib, sorafenib, nab-palitaxel, a derivative or a combination thereof. In one embodiment, the therapeutic agent may include capecitabine, cisplatin, Cyclophosphamide, methotrexate, 5-fluorouracil, Doxorubicin, cyclophosphamide, Mustine, vincristine, procarbazine, prednisolone, bleomycin, vinblastine, dacarbazine, etoposide, Epirubicin, pemetrexed, folinic acid, gemicitabine, oxaliplatin, irinotemay, topotemay, camptothecin, docetaxel, paclitaxel,, fulvestrant, tamoxifen, letrozole, exemestane, anastrozole, aminoglutethimide, testolactone, vorozole, formestane, fadrozole, letrozole, erlotinib, lafatinib, dasatinib, gefitinib, osimertinib, vandertanib, afatinib, imatinib, pazopinib, lapatinib, sunitinib, nilotinib, sorafenib, nab-palitaxel, Everolimus, temsirolimus, Dabrafenib, vemurafenib, trametinib, vintafolide, apatinib, crizotinib, perifosine, olaparib, Bortezomib, tofacitinib, a derivative or a combination thereof.

Cancers, including breast cancer, colorectal cancer, pancreatic cancer, head and neck cancer, melanoma, ovarian cancer, prostate cancer, non-small lung cell cancer, glioma, esophageal cancer, nasopharyngeal cancer, anal cancer, rectal cancer, gastric cancer, bladder cancer, cervical cancer, or brain cancer, may express cancer-associated genes. Inhibition of cancer-associated activity with specific monoclonal antibodies or antigen-binding fragment may have therapeutic effect on cancers. Furthermore, administering a therapeutically effective amount of composition comprising monoclonal antibodies or antigen-binding fragment specific for cancer-associated protein may cure, prevent, ameliorate, and delay the development or metastasis of cancers, through the effect of the cytotoxic agent.

The present disclosure may be understood more readily by reference to the following detailed description of specific embodiments and examples included herein. Although the present disclosure has been described with reference to specific details of certain embodiments thereof, it is not intended that such details should be regarded as limitations upon the scope of the disclosure.

Examples

Figure 2:
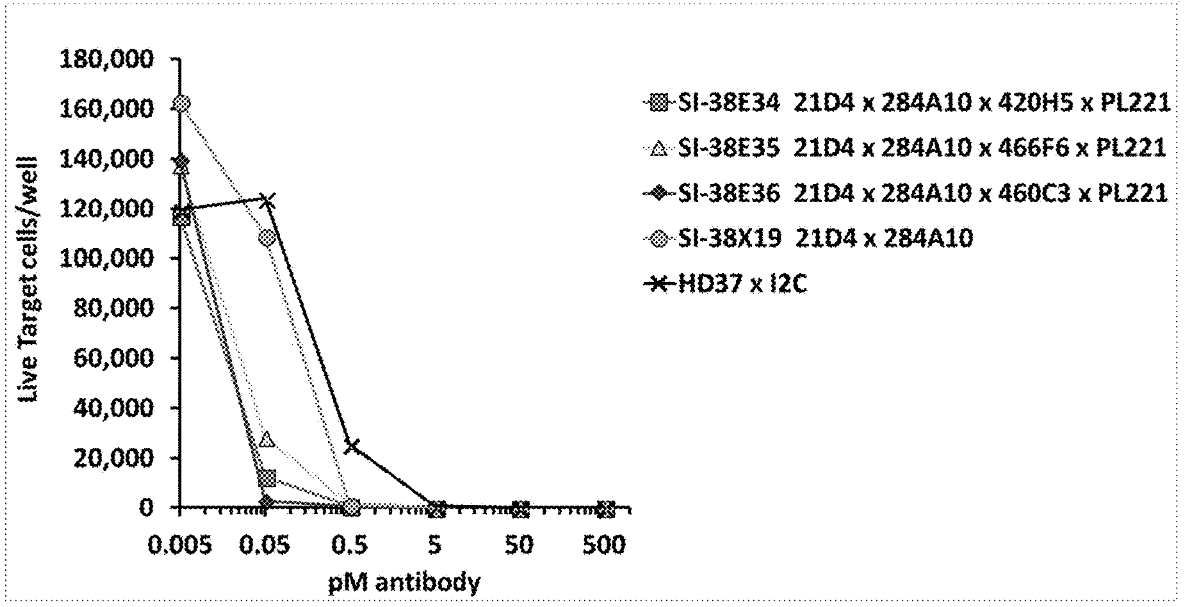
FIG. 2 depicts experiment results showing re-directed T cell cytotoxicity (RTCC) assay with PBMC (peripheral blood mononuclear cells) as effectors and B-Acute Lymphoblastic Leukemia (B-ALL) cell line Kasumi-2 as targets
Figure 3:
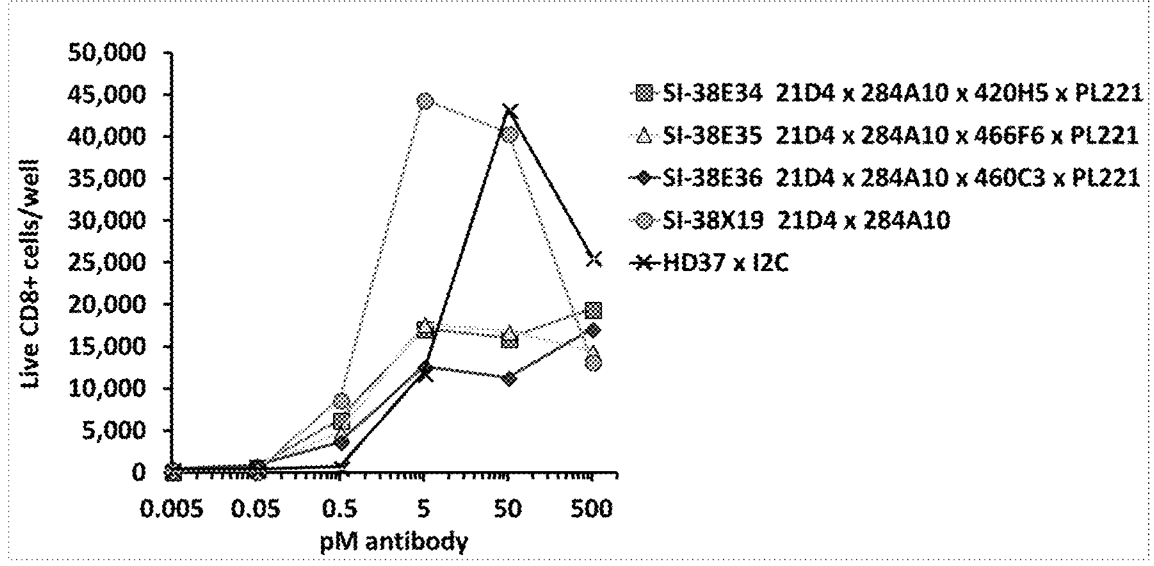
FIG. 3 depicts experiment results showing proliferation of CD8+ T cells induced by tetra-specific GNC antibodies
Figure 4:
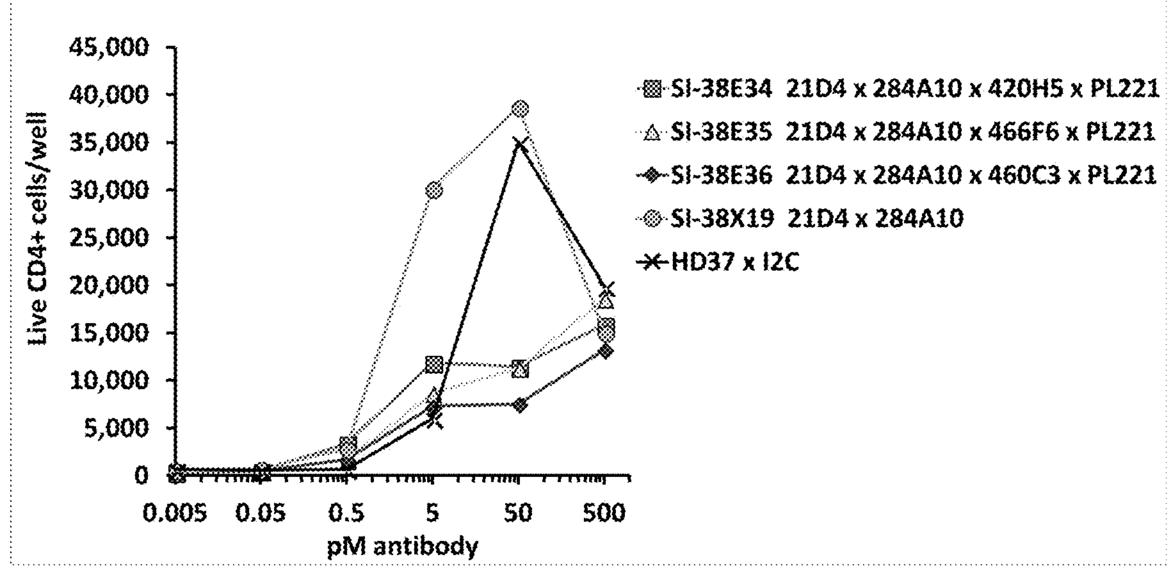
FIG. 4 depicts experiment results showing proliferation of CD4+ T cells induced by tetra-specific GNC antibodies
Figure 5:
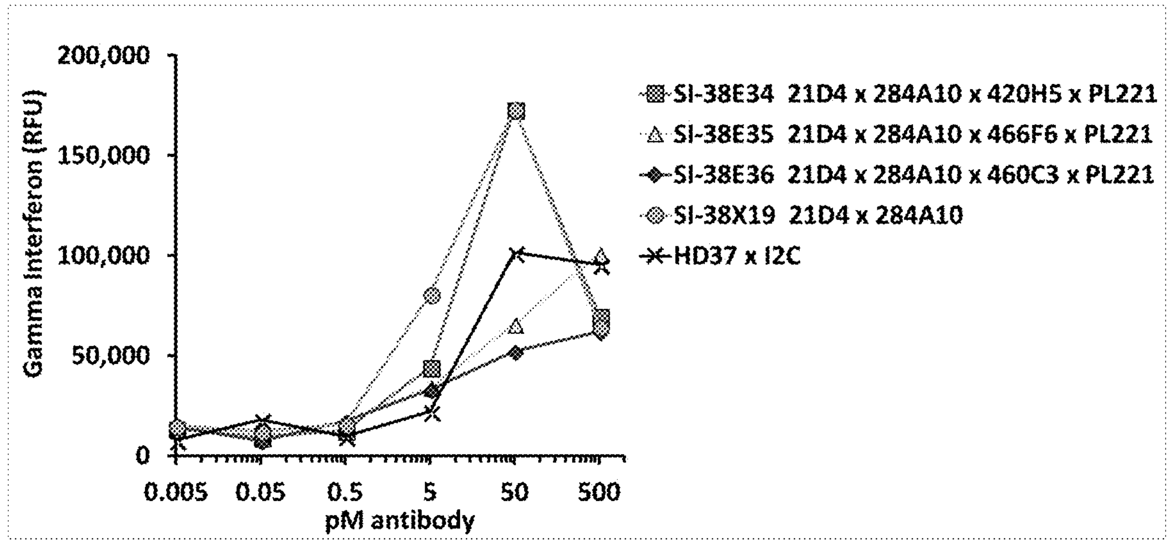
FIG. 5 depicts experiment results showing secretion of Gamma Interferon from PBMC induced by tetra-specific GNC antibodies

Example 1: Re-Directed T Cell Cytotoxicity (RTCC) Assay with PBMC (Peripheral Blood Mononuclear Cells) as Effectors and B-Acute Lymphoblastic Leukemia (B-ALL) Cell Lines Kasumi-2 and NALM-6 as Targets The Tetra-specific antibodies listed in tables 1 and 2 were tested for RTCC activity against the B-ALL cell lines Kasumi-2 and Nalm-6 using human PBMC as effectors. Both the Kasumi-2 and Nalm-6 target cells were previously transfected with green fluorescent protein (GFP) and FACS-sorted to create a population of cells where greater than 99% expressed GFP. The GFP+Kasumi-2 and GFP+Nalm-6 cells were counted and set to a density of 100,000 cells/ml in assay media. Human PBMC were counted and set to a density of 100,000 cells/ml. Antibodies were prepared at 2X final concentration and titrated 1:10 across 6 wells of a 96 well plate in assay media. In the destination 96 well plate the target cells, PBMC, and serially titrated antibodies were combined by adding 50 μl of target cells (5,000), 50 μl of PBMC cells (5,000), and 100 μl of each antibody dilution to each well of the assay. The assay plate was incubated at 37 C for 8 days and then 100 μl of supernatant was transferred into a new 96 well and frozen at −80C for later analysis. The cells were re-suspended by pipetting and transferred to a 384 well plate. Cells were stained with an antibody cocktail that included anti-CD4 and anti-CD8 directly conjugated commercial antibodies. The cells remaining in the wells were washed and re-suspended in assay buffer containing anti-CD4 (biolegend Cat #317436) and anti-CD8 (biolegend Cat #557746) directly conjugated commercial antibodies plus 7AAD live/dead stain and counting beads and then analyzed on a BD LSRII Fortessa. The number of CD4+, CD8+ and GFP+target cells per well were determined. As shown in FIG. 2, the tetra-specific antibodies SI-38×34, 35, and 36 induce T cell killing of most of the target NALM-6 cells at a concentration of 0.05 μM which is roughly 10-fold more potent than the bi-specific antibodies SI-38×19 and HD37×12C. Since the bi-specific SI-38×19 has the 21D4 (CD19) and 284A10 (CD3) binding domains as in the tetra-specific antibodies SI-38E34, 35, and 36 but the tetra-specific antibodies have the additional domains of 420H5, 466F6, 460C3 (41BB) and PL221 (PDL1) this suggests that the additional 41BB and/or PDL1 binding domains in the tetra-specific antibodies have an enhancing effect on T cell killing of the target cells. In addition, as shown in FIG. 3 the bi-specific antibody 21D4×284A10 strongly induces proliferation of CD8+ T cells as does the bi-specific HD37×12C at 10-fold higher concentration than the 21D4×284A10 bid-specific. However, the tetra-specific antibodies SI-38E34, 35, and 36 induce much lower levels of CD8+ T cell proliferation at similar concentrations. These data, combined with the RTCC data in FIG. 2 suggest that the tetra-specific antibodies induce differentiation of CD8+ T cells into terminal cytotoxic T cells better than the bi-specific antibodies. As shown in FIG. 4, the bi-specific antibodies tested also induce greater proliferation of CD4+ T cells, similar to the effect on proliferation of CD8+ T cells, and the tetra-specific antibodies induce much lower levels of CD4+ T cell proliferation.

Figure 6:
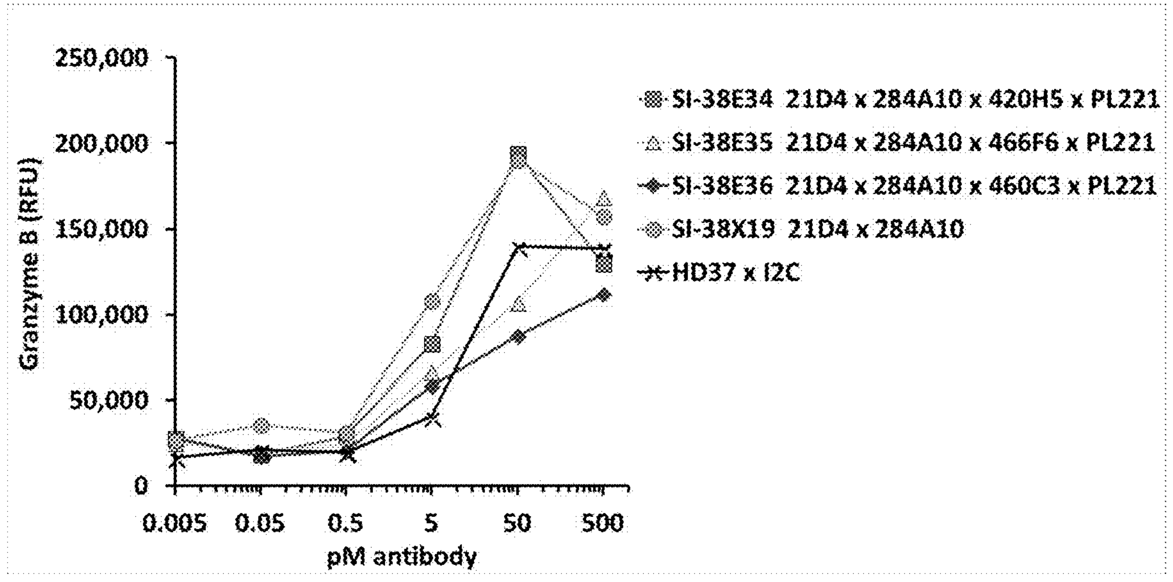
FIG. 6 depicts experiment results showing secretion of Granzyme B from PBMC induced by tetra-specific GNC antibodies

Example 2: ELISA Analysis of Gamma Interferon and Granzyme B in the Culture Supernatants from Day 8 RTCC with CD19-Specific GNC Antibodies The well supernatants that were stored at −80 were thawed and analyzed for the level of interferon gamma and granzyme B using the g-IFN and GrB kits from R&D systems (no.DY285B and no.DY2906-05) as per the manufacturers recommended protocol. QuantaRed™ Enhanced Chemifluorescent HRP Substrate (ThermoFisher Scientific no. 15159) was added to each well of the ELISA plates and used as per the manufactures instructions. As shown in FIG. 6, the bi-specific 21D4×284A10 induced a high level of gamma interferon secretion from PBMC at 50 μM of antibody, almost identical to the tetra-specific antibody SI-34E34, whereas the other tetra-specific antibodies SI-34E35 and 36 as well as the bi-specific HD37×12C did induce gamma interferon secretion from PBMC but a much lower levels. As shown in FIG. 6, the bi-specific 21D4×284A10 induced a high level of granzyme B secretion from PBMC at 50 μM of antibody, almost identical to the tetra-specific antibody SI-34E34, whereas the other tetra-specific antibodies SI-34E35 and 36 as well as the bi-specific HD37×12C did induce granzyme B secretion from PBMC but at slightly lower levels. While the tumor cell killing mediated by the tetra-specific antibodies SI-38E34, 35, and 36 was quite similar as shown in FIG. 3, the amount of granzyme B secreted from PBMC was highest with the tetra-specific antibody SI-38E34 at about 2-fold higher levels compare to the other 2 tetra-specific antibodies SI-38E35 and 36.

While the present disclosure has been described with reference to particular embodiments or examples, it may be understood that the embodiments are illustrative and that the disclosure scope is not so limited. Alternative embodiments of the present disclosure may become apparent to those having ordinary skill in the art to which the present disclosure pertains. Such alternate embodiments are considered to be encompassed within the scope of the present disclosure. Accordingly, the scope of the present disclosure is defined by the appended claims and is supported by the foregoing description. All references cited or referred to in this disclosure are hereby incorporated by reference in their entireties.

MULTI-SPECIFIC ANTIBODIES AND METHODS OF MAKING AND USING THEREOF SEQUENCE LISTING tetra-specific sequence listing
CDR's underlined in amino acid sequences
anti-CD3 284A10 VHv1 nt

>SEQ ID: 01

GAGGTGCAGCTGGTGGAGTCTGGGGGAGGCTTGGTCCAGCCTGGGGGGTCCCTGAGACTCTCCTGTGCAGCCTC

TGGATTCACCATCAGTACCAATGCAATGAGCTGGGTCCGCCAGGCTCCAGGGAAGGGGCTGGAGTGGATCGGAG

TCATTACTGGTCGTGATATCACATACTACGCGAGCTGGGCGAAAGGCAGATTCACCATCTCCAGAGACAATTCC

AAGAACACGCTGTATCTTCAAATGAACAGCCTGAGAGCCGAGGACACGGCTGTGTATTACTGTGCGCGCGACGG

TGGATCATCTGCTATTACTAGTAACAACATTTGGGGCCAAGGAACTCTGGTCACCGTTTCTTCA anti-CD3 284A10 VHv1 aa

>SEQ ID: 02

EVQLVESGGGLVQPGGSLRLSCAASGFTISTNAMSWVRQAPGKGLEWIGVITGRDITYYASWAKGRFTISRDNS

KNTLYLQMNSLRAEDTAVYYCARDGGSSAITSNNIWGQGTLVTVSS anti-CD3 284A10 VLv1 nt

>SEQ ID: 03

GACGTCGTGATGACCCAGTCTCCTTCCACCCTGTCTGCATCTGTAGGAGACAGAGTCACCATCAATTGCCAAGC

CAGTGAGAGCATTAGCAGTTGGTTAGCCTGGTATCAGCAGAAACCAGGGAAAGCCCCTAAGCTCCTGATCTATG

AAGCATCCAAACTGGCATCTGGGGTCCCATCAAGGTTCAGCGGCAGTGGATCTGGGACAGAGTTCACTCTCACC

ATCAGCAGCCTGCAGCCTGATGATTTTGCAACTTATTACTGCCAAGGCTATTTTTATTTTATTAGTCGTACTTA

TGTAAATTCTTTCGGCGGAGGGACCAAGGTGGAGATCAAA anti-CD3 284A10 VLv1 aa

>SEQ ID: 04

DVVMTQSPSTLSASVGDRVTINCQASESISSWLAWYQQKPGKAPKLLIYEASKLASGVPSRFSGSGSGTEFTLT

ISSLQPDDFATYYCQGYEYEISRTYVNSEGGGTKVEIK anti-CD3 I2C VH nt

>SEQ ID: 05

CAGGTGCAATTGGTGGAAAGCGGAGGGGGACTGGTGCAGCCCGGGGGAAGTCTGAAGCTGTCCTGTGCCGCCAG

CGGCTTTACCTTCAACAAGTACGCCATGAATTGGGTCCGACAGGCCCCAGGGAAAGGCCTGGAATGGGTGGCAC

GGATTCGGTCCAAGTACAACAACTACGCCACCTACTACGCTGACTCCGTGAAGGACAGATTCACCATCAGCCGG

GACGACTCTAAGAACACCGCCTATCTGCAGATGAACAACCTGAAAACCGAGGATACAGCTGTGTACTATTGTGT

GCGGCACGGCAACTTCGGCAACTCCTACATCTCCTACTGGGCCTATTGGGGACAGGGAACACTGGTCACCGTGT

CTAGC anti-CD3 I2C VH aa

>SEQ ID: 06

QVQLVESGGGLVQPGGSLKLSCAASGFTFNKYAMNWVRQAPGKGLEWVARIRSKYNNYATYYADSVKDRFTISR

DDSKNTAYLQMNNLKTEDTAVYYCVRHGNFGNSYISYWAYWGQGTLVTVSS anti-CD3 I2C VL nt

>SEQ ID: 07

CAGACCGTGGTCACCCAGGAACCTTCCCTGACCGTCTCCCCAGGCGGCACCGTGACCCTGACCTGTGGCTCCTC

TACCGGCGCTGTGACCTCCGGCAACTACCCTAACTGGGTGCAGCAGAAACCCGGACAGGCTCCTAGAGGCCTGA

TCGGCGGCACCAAGTTTCTGGCCCCTGGCACCCCTGCCAGATTCTCCGGCTCCCTGCTGGGAGGCAAGGCCGCT

CTGACCCTGTCTGGCGTGCAGCCTGAGGACGAGGCCGAGTACTACTGTGTGCTGTGGTACTCCAACAGATGGGT

GTTCGGAGGCGGCACAAAGCTGACCGTGCTGTCCTCG anti-CD3 I2C VL aa

>SEQ ID: 08

QTVVTQEPSLTVSPGGTVTLTCGSSTGAVTSGNYPNWVQQKPGQAPRGLIGGTKFLAPGTPARFSGSLLGGKAA

LTLSGVQPEDEAEYYCVLWYSNRWVFGGGTKLTVLSS

-continued anti-PD-L1 PL221G5 VHv1 nt

>SEQ ID: 09

GAGGTGCAGCTGTTGGAGTCTGGGGGAGGCTTGGTACAGCCTGGGGGGTCCCTGAGACTCTCCTGTGCAGCCTC

TGGATTCTCCTTCAGTAGCGGGTACGACATGTGCTGGGTCCGCCAGGCTCCAGGGAAGGGGCTGGAGTGGATCG

CATGCATTGCTGCTGGTAGTGCTGGTATCACTTACGACGCGAACTGGGCGAAAGGCCGGTTCACCATCTCCAGA

GACAATTCCAAGAACACGCTGTATCTGCAAATGAACAGCCTGAGAGCCGAGGACACGGCCGTATATTACTGTGC

GAGATCGGCGTTTTCGTTCGACTACGCCATGGACCTCTGGGGCCAGGGAACCCTGGTCACCGTCTCGAGC anti-PD-L1 PL221G5 VHv1 aa

>SEQ ID: 10

EVQLLESGGGLVQPGGSLRLSCAASGFSFSSGYDMCWVRQAPGKGLEWIACIAAGSAGITYDANWAKGRFTISR

DNSKNTLYLQMNSLRAEDTAVYYCARSAFSFDYAMDLWGQGTLVTVSS anti-PD-L1 PL221G5 VLv1 nt

>SEQ ID: 11

GACATCCAGATGACCCAGTCTCCTTCCACCCTGTCTGCATCTGTAGGAGACAGAGTCACCATCACTTGCCAGGC

CAGTCAGAGCATTAGTTCCCACTTAAACTGGTATCAGCAGAAACCAGGGAAAGCCCCTAAGCTCCTGATCTATA

AGGCATCCACTCTGGCATCTGGGGTCCCATCAAGGTTCAGCGGCAGTGGATCTGGGACAGAATTTACTCTCACC

ATCAGCAGCCTGCAGCCTGATGATTTTGCAACTTATTACTGCCAACAGGGTTATAGTTGGGGTAATGTTGATAA

TGTTTTCGGCGGAGGGACCAAGGTGGAGATCAAA anti-PD-L1 PL221G5 VLv1 aa

>SEQ ID: 12

DIQMTQSPSTLSASVGDRVTITCQASQSISSHLNWYQQKPGKAPKLLIYKASTLASGVPSRFSGSGSGTEFTLT

ISSLQPDDFATYYCQQGYSWGNVDNVFGGGTKVEIK anti-4-1BB 420H5 VHv3 nt

>SEQ ID: 13

CAGTCGCTGGTGGAGTCTGGGGGAGGCTTGGTACAGCCTGGGGGGTCCCTGAGACTCTCCTGTGCAGCCTCTGG

ATTCTCCTTCAGTAGCAACTACTGGATATGCTGGGTCCGCCAGGCTCCAGGGAAGGGGCTGGAGTGGATCGCAT

GCATTTATGTTGGTAGTAGTGGTGACACTTACTACGCGAGCTCCGCGAAAGGCCGGTTCACCATCTCCAGAGAC

AATTCCAAGAACACGCTGTATCTGCAAATGAACAGCCTGAGAGCCGAGGACACGGCCGTATATTACTGTGCGAG

AGATAGTAGTAGTTATTATATGTTTAACTTGTGGGGCCAGGGAACCCTGGTCACCGTCTCGAGC anti-4-1BB 420H5 VHv3 aa

>SEQ ID: 14

QSLVESGGGLVQPGGSLRLSCAASGFSFSSNYWICWVRQAPGKGLEWIACIYVGSSGDTYYASSAKGRFTISRD

NSKNTLYLQMNSLRAEDTAVYYCARDSSSYYMFNLWGQGTLVTVSS anti-4-1BB 420H5 VLv3 nt

>SEQ ID: 15

GCCCTTGTGATGACCCAGTCTCCTTCCACCCTGTCTGCATCTGTAGGAGACAGAGTCACCATCAATTGCCAGGC

CAGTGAGGACATTGATACCTATTTAGCCTGGTATCAGCAGAAACCAGGGAAAGCCCCTAAGCTCCTGATCTTTT

ATGCATCCGATCTGGCATCTGGGGTCCCATCAAGGTTCAGCGGCAGTGGATCTGGGACAGAATTCACTCTCACC

ATCAGCAGCCTGCAGCCTGATGATTTTGCAACTTATTACTGCCAAGGCGGTTACTATACTAGTAGTGCTGATAC

GAGGGGTGCTTTCGGCGGAGGGACCAAGGTGGAGATCAAA anti-4-1BB 420H5 VLv3 aa

>SEQ ID: 16

ALVMTQSPSTLSASVGDRVTINCQASEDIDTYLAWYQQKPGKAPKLLIFYASDLASGVPSRFSGSGSGTEFTLT

ISSLQPDDFATYYCQGGYYTSSADTRGAFGGGTKVEIK anti-4-1BB 466F6 VHv2 nt

>SEQ ID: 17

CGGTCGCTGGTGGAGTCTGGGGGAGGCTTGGTCCAGCCTGGGGGGTCCCTGAGACTCTCCTGTACAGCCTCTGG

ATTCACCATCAGTAGCTACCACATGCAGTGGGTCCGCCAGGCTCCAGGGAAGGGGCTGGAGTACATCGGAACCA

TTAGTAGTGGTGGTAATGTATACTACGCGAGCTCCGCGAGAGGCAGATTCACCATCTCCAGACCCTCGTCCAAG

-continued

AACACGGTGGATCTTCAAATGAACAGCCTGAGAGCCGAGGACACGGCTGTGTATTACTGTGCGAGAGACTCTGG

TTATAGTGATCCTATGTGGGGCCAGGGAACCCTGGTCACCGTCTCGAGC anti-4-1BB 466F6 VHv2 aa

>SEQ ID: 18

RSLVESGGGLVQPGGSLRLSCTASGFTISSYHMQWVRQAPGKGLEYIGTISSGGNVYYASSARGRFTISRPSSK

NTVDLQMNSLRAEDTAVYYCARDSGYSDPMWGQGTLVTVSS anti-4-1BB 466F6 VLv5 nt

>SEQ ID: 19

GACGTTGTGATGACCCAGTCTCCATCTTCCGTGTCTGCATCTGTAGGAGACAGAGTCACCATCACCTGTCAGGC

CAGTCAGAACATTAGGACTTACTTATCCTGGTATCAGCAGAAACCAGGGAAAGCCCCTAAGCTCCTGATCTATG

CTGCAGCCAATCTGGCATCTGGGGTCCCATCAAGGTTCAGCGGCAGTGGATCTGGGACAGATTTCACTCTCACC

ATCAGCGACCTGGAGCCTGGCGATGCTGCAACTTACTATTGTCAGTCTACCTATCTTGGTACTGATTATGTTGG

CGGTGCTTTCGGCGGAGGGACCAAGGTGGAGATCAAA anti-4-1BB 466F6 VLv5 aa

>SEQ ID: 20

DVVMTQSPSSVSASVGDRVTITCQASQNIRTYLSWYQQKPGKAPKLLIYAAANLASGVPSRFSGSGSGTDFTLT

ISDLEPGDAATYYCQSTYLGTDYVGGAFGGGTKVEIK anti-4-1BB 460C3 VHv1 nt

>SEQ ID: 21

GAGGTGCAGCTGTTGGAGTCTGGGGGAGGCTTGGTACAGCCTGGGGGGTCCCTGAGACTCTCCTGTGCAGCCTC

TGGAATCGACTTCAGTAGGAGATACTACATGTGCTGGGTCCGCCAGGCTCCAGGGAAGGGGCTGGAGTGGATCG

CATGCATATATACTGGTAGCCGCGATACTCCTCACTACGCGAGCTCCGCGAAAGGCCGGTTCACCATCTCCAGA

GACAATTCCAAGAACACGCTGTATCTGCAAATGAACAGCCTGAGAGCCGAGGACACGGCCGTATATTACTGTGC

GAGAGAAGGTAGCCTGTGGGGCCAGGGAACCCTGGTCACCGTCTCGAGC anti-4-1BB 460C3 VHv1 aa

>SEQ ID: 22

EVQLLESGGGLVQPGGSLRLSCAASGIDFSRRYYMCWVRQAPGKGLEWIACIYTGSRDTPHYASSAKGRFTISR

DNSKNTLYLQMNSLRAEDTAVYYCAREGSLWGQGTLVTVSS anti-4-1BB 460C3 VLv1 nt

>SEQ ID: 23

GACATCCAGATGACCCAGTCTCCTTCCACCCTGTCTGCATCTGTAGGAGACAGAGTCACCATCACTTGCCAGTC

CAGTCAGAGTGTTTATAGTAACTGGTTCTCCTGGTATCAGCAGAAACCAGGGAAAGCCCCTAAGCTCCTGATCT

ATTCTGCATCCACTCTGGCATCTGGGGTCCCATCAAGGTTCAGCGGCAGTGGATCTGGGACAGAATTCACTCTC

ACCATCAGCAGCCTGCAGCCTGATGATTTTGCAACTTATTACTGCGCAGGCGGTTACAATACTGTTATTGATAC

TTTTGCTTTCGGCGGAGGGACCAAGGTGGAGATCAAA anti-4-1BB 460C3 VLv1 aa

>SEQ ID: 24

DIQMTQSPSTLSASVGDRVTITCQSSQSVYSNWFSWYQQKPGKAPKLLIYSASTLASGVPSRFSGSGSGTEFTL

TISSLQPDDFATYYCAGGYNTVIDTFAFGGGTKVEIK anti-CD19 21D4 VH nt

>SEQ ID: 25

GAGGTGCAGCTGGTGCAGTCTGGAGCAGAGGTGAAGAAACCAGGAGAGTCTCTGAAGATCTCCTGTAAGGGTTC

TGGATACAGCTTTAGCAGTTCATGGATCGGCTGGGTGCGCCAGGCACCTGGGAAAGGCCTGGAATGGATGGGGA

TCATCTATCCTGATGACTCTGATACCAGATACAGTCCATCCTTCCAAGGCCAGGTCACCATCTCAGCCGACAAG

TCCATCAGGACTGCCTACCTGCAGTGGAGTAGCCTGAAGGCCTCGGACACCGCTATGTATTACTGTGCGAGACA

TGTTACTATGATTTGGGGAGTTATTATTGACTTCTGGGGCCAGGGAACCCTGGTCACCGTCTCCTCA anti-CD19 21D4 VH aa

>SEQ ID: 26

EVQLVQSGAEVKKPGESLKISCKGSGYSFSSSWIGWVRQAPGKGLEWMGIIYPDDSDTRYSPSFQGQVTISADK

SIRTAYLQWSSLKASDTAMYYCARHVTMIWGVIIDFWGQGTLVTVSS

-continued anti-CD19 21D4 VL nt

>SEQ ID: 27

GCCATCCAGTTGACCCAGTCTCCATCCTCCCTGTCTGCATCTGTAGGAGACAGAGTCACCATCACTTGCCGGGC

AAGTCAGGGCATTAGCAGTGCTTTAGCCTGGTATCAGCAGAAACCAGGGAAAGCTCCTAAGCTCCTGATCTATG

ATGCCTCCAGTTTGGAAAGTGGGGTCCCATCAAGGTTCAGCGGCAGTGGATCTGGGACAGATTTCACTCTCACC

ATCAGCAGCCTGCAGCCTGAAGATTTTGCAACTTATTACTGTCAACAGTTTAATAGTTACCCATTCACTTTCGG

CCCTGGGACCAAAGTGGATATCAAA anti-CD19 Z1D4 VL aa

>SEQ ID 28

AIQLTQSPSSLSASVGDRVTITCRASQGISSALAWYQQKPGKAPKLLIYDASSLESGVPSRFSGSGSGTDFTLT

ISSLQPEDFATYYCQQFNSYPFTFGPGTKVDIK anti-CD19 HD37 VH nt

>SEQ ID: 29

CAGGTCCAACTCCAGCAGTCTGGGGCTGAGCTGGTGAGGCCTGGGTCCTCAGTGAAGATTTCCTGCAAGGCTTC

TGGCTATGCCTTCAGTAGCTACTGGATGAACTGGGTGAAGCAGAGGCCTGGACAGGGTCTTGAGTGGATTGGAC

AGATTTGGCCTGGAGATGGTGATACTAACTACAATGGAAAGTTCAAGGGGAAAGCCACTCTGACTGCAGACGAA

TCCTCCAGCACAGCCTACATGCAACTCAGCAGCCTAGCATCTGAGGACTCTGCGGTCTATTTCTGTGCAAGACG

GGAGACTACGACGGTAGGCCGTTATTACTATGCTATGGACTACTGGGGCCAAGGGACCACGGTCACCGTCTCCT

CC anti-CD19 HD37 VH aa

>SEQ ID: 30

QVQLQQSGAELVRPGSSVKISCKASGYAFSSYWMNWVKQRPGQGLEWIGQIWPGDGDTNYNGKFKGKATLTADE

SSSTAYMQLSSLASEDSAVYFCARRETTTVGRYYYAMDYWGQGTTVTVSS anti-CD19 HD37 VL nt

>SEQ ID: 31

GATATCCAGCTGACCCAGTCTCCAGCTTCTTTGGCTGTGTCTCTAGGGCAGAGGGCCACCATCTCCTGCAAGGC

CAGCCAAAGTGTTGATTATGATGGTGTGAGTTACTTGAACTGGTATCAACAGATTCCAGGACAGCCACCCAAAC

TCCTCATCTATGATGCTTCCAATCTAGTTTCTGGGATCCCACCCAGGTTTAGTGGCAGTGGGTCTGGGACAGAC

TTCACCCTCAACATCCATCCTGTGGAGAAGGTGGATGCTGCAACCTATCACTGTCAGCAAAGTACTGAGGATCC

GTGGACGTTCGGTGGAGGGACCAAGCTCGAGATTAAA anti-CD19 HD37 VL nt

>SEQ ID: 32

DIQLTQSPASLAVSLGQRATISCKASQSVDYDGVSYLNWYQQIPGQPPKLLIYDASNLVSGIPPRFSGSGSGTD

FTLNIHPVEKVDAATYHCQQSTEDPWTFGGGTKLEIK human IgG1 null (G1m-fa with ADCC/CDC null mutations) nt

>SEQ ID: 33

GCTAGCACCAAGGGCCCATCGGTCTTCCCCCTGGCACCCTCCTCCAAGAGCACCTCTGGGGGCACAGCGGCCCT

GGGCTGCCTGGTCAAGGACTACTTCCCCGAACCGGTGACGGTGTCGTGGAACTCAGGCGCCCTGACCAGCGGCG

TGCACACCTTCCCGGCTGTCCTACAGTCCTCAGGACTCTACTCCCTCAGCAGCGTGGTGACCGTGCCCTCCAGC

AGCTTGGGCACCCAGACCTACATCTGCAACGTGAATCACAAGCCCAGCAACACCAAGGTGGACAAGAGAGTTGA

GCCCAAATCTTGTGACAAAACTCACACATGCCCACCGTGCCCAGCACCTGAAGCCGCGGGGGCACCGTCAGTCT

TCCTCTTCCCCCCAAAACCCAAGGACACCCTCATGATCTCCCGGACCCCTGAGGTCACATGCGTGGTGGTGGAC

GTGAGCCACGAAGACCCTGAGGTCAAGTTCAACTGGTACGTGGACGGCGTGGAGGTGCATAATGCCAAGACAAA

GCCGCGGGAGGAGCAGTACAACAGCACGTACCGTGTGGTCAGCGTCCTCACCGTCCTGCACCAGGACTGGCTGA

ATGGCAAGGAGTACAAGTGCGCGGTCTCCAACAAAGCCCTCCCAGCCCCCATCGAGAAAACCATCTCCAAAGCC

AAAGGGCAGCCCCGAGAACCACAGGTGTACACCCTGCCCCCATCCCGGGATGAGCTGACCAAGAACCAGGTCAG

CCTGACCTGCCTGGTCAAAGGCTTCTATCCCAGCGACATCGCCGTGGAGTGGGAGAGCAATGGGCAGCCGGAGA

-continued

ACAACTACAAGACCACGCCTCCCGTGCTGGACTCCGACGGCTCCTTCTTCCTCTATAGCAAGCTCACCGTGGAC

AAGAGCAGGTGGCAGCAGGGGAACGTCTTCTCATGCTCCGTGATGCATGAGGCTCTGCACAACCACTACACGCA

GAAGAGCCTCTCCCTGTCTCCGGGT human IgG1 null (G1m-fa with ADCC/CDC null mutations) aa

>SEQ ID: 34

ASTKGPSVFPLAPSSKSTSGGTAALGCLVKDYFPEPVTVSWNSGALTSGVHTFPAVLQSSGLYSLSSVVTVPSS

SLGTQTYICNVNHKPSNTKVDKRVEPKSCDKTHTCPPCPAPEAAGAPSVFLFPPKPKDTLMISRTPEVTCVVVD

VSHEDPEVKFNWYVDGVEVHNAKTKPREEQYNSTYRVVSVLTVLHQDWLNGKEYKCAVSNKALPAPIEKTISKA

KGQPREPQVYTLPPSRDELTKNQVSLTCLVKGFYPSDIAVEWESNGQPENNYKTTPPVLDSDGSFFLYSKLTVD

KSRWQQGNVFSCSVMHEALHNHYTQKSLSLSPG human Ig Kappa nt

>SEQ ID: 35

CGTACGGTGGCTGCACCATCTGTCTTCATCTTCCCGCCATCTGATGAGCAGTTGAAATCTGGAACTGCCTCTGT

TGTGTGCCTGCTGAATAACTTCTATCCCAGAGAGGCCAAAGTACAGTGGAAGGTGGATAACGCCCTCCAATCGG

GTAACTCCCAGGAGAGTGTCACAGAGCAGGACAGCAAGGACAGCACCTACAGCCTCAGCAGCACCCTGACGCTG

AGCAAAGCAGACTACGAGAAACACAAAGTCTACGCCTGCGAAGTCACCCATCAGGGCCTGAGCTCGCCCGTCAC

AAAGAGCTTCAACAGGGGAGAGTGT human Ig Kappa aa

>SEQ ID: 36

RTVAAPSVFIFPPSDEQLKSGTASVVCLLNNFYPREAKVQWKVDNALQSGNSQESVTEQDSKDSTYSLSSTLTL

SKADYEKHKVYACEVTHQGLSSPVTKSFNRGEC

SI-38E34 (21D4-LH-scFv x 284A10-L1H1-scFv x 420H5-Fab x PL221G5-H1L1-scFv) heavy chain nt

>SEQ ID: 37

GCCATCCAGTTGACCCAGTCTCCATCCTCCCTGTCTGCATCTGTAGGAGACAGAGTCACCATCACTTGCCGGGC

AAGTCAGGGCATTAGCAGTGCTTTAGCCTGGTATCAGCAGAAACCAGGGAAAGCTCCTAAGCTCCTGATCTATG

ATGCCTCCAGTTTGGAAAGTGGGGTCCCATCAAGGTTCAGCGGCAGTGGATCTGGGACAGATTTCACTCTCACC

ATCAGCAGCCTGCAGCCTGAAGATTTTGCAACTTATTACTGTCAACAGTTTAATAGTTACCCATTCACTTTCGG

CCCTGGGACCAAAGTGGATATCAAAGGCGGTGGCGGTAGTGGGGGAGGCGGTTCTGGCGGCGGAGGGTCCGGCG

GTGGAGGATCAGAGGTGCAGCTGGTGCAGTCTGGAGCAGAGGTGAAGAAACCAGGAGAGTCTCTGAAGATCTCC

TGTAAGGGTTCTGGATACAGCTTTAGCAGTTCATGGATCGGCTGGGTGCGCCAGGCACCTGGGAAAGGCCTGGA

ATGGATGGGGATCATCTATCCTGATGACTCTGATACCAGATACAGTCCATCCTTCCAAGGCCAGGTCACCATCT

CAGCCGACAAGTCCATCAGGACTGCCTACCTGCAGTGGAGTAGCCTGAAGGCCTCGGACACCGCTATGTATTAC

TGTGCGAGACATGTTACTATGATTTGGGGAGTTATTATTGACTTCTGGGGCCAGGGAACCCTGGTCACCGTCTC

CTCAGGCGGTGGAGGGTCCGGCGGTGGTGGATCCGACGTCGTGATGACCCAGTCTCCTTCCACCCTGTCTGCAT

CTGTAGGAGACAGAGTCACCATCAATTGCCAAGCCAGTGAGAGCATTAGCAGTTGGTTAGCCTGGTATCAGCAG

AAACCAGGGAAAGCCCCTAAGCTCCTGATCTATGAAGCATCCAAACTGGCATCTGGGGTCCCATCAAGGTTCAG

CGGCAGTGGATCTGGGACAGAGTTCACTCTCACCATCAGCAGCCTGCAGCCTGATGATTTTGCAACTTATTACT

GCCAAGGCTATTTTTATTTTATTAGTCGTACTTATGTAAATTCTTTCGGCGGAGGGACCAAGGTGGAGATCAAA

GGCGGTGGCGGTAGTGGGGGAGGCGGTTCTGGCGGCGGAGGGTCCGGCGGTGGAGGATCAGAGGTGCAGCTGGT

GGAGTCTGGGGGAGGCTTGGTCCAGCCTGGGGGGTCCCTGAGACTCTCCTGTGCAGCCTCTGGATTCACCATCA

GTACCAATGCAATGAGCTGGGTCCGCCAGGCTCCAGGGAAGGGGCTGGAGTGGATCGGAGTCATTACTGGTCGT

GATATCACATACTACGCGAGCTGGGCGAAAGGCAGATTCACCATCTCCAGAGACAATTCCAAGAACACGCTGTA

TCTTCAAATGAACAGCCTGAGAGCCGAGGACACGGCTGTGTATTACTGTGCGCGCGACGGTGGATCATCTGCTA

TTACTAGTAACAACATTTGGGGCCAAGGAACTCTGGTCACCGTTTCTTCAGGCGGTGGAGGGTCCGGAGGTGGT

-continued

GGCTCCCAGTCGCTGGTGGAGTCTGGGGGAGGCTTGGTACAGCCTGGGGGGTCCCTGAGACTCTCCTGTGCAGC

CTCTGGATTCTCCTTCAGTAGCAACTACTGGATATGCTGGGTCCGCCAGGCTCCAGGGAAGGGGCTGGAGTGGA

TCGCATGCATTTATGTTGGTAGTAGTGGTGACACTTACTACGCGAGCTCCGCGAAAGGCCGGTTCACCATCTCC

AGAGACAATTCCAAGAACACGCTGTATCTGCAAATGAACAGCCTGAGAGCCGAGGACACGGCCGTATATTACTG

TGCGAGAGATAGTAGTAGTTATTATATGTTTAACTTGTGGGGCCAGGGAACCCTGGTCACCGTCTCGAGCGCTA

GCACCAAGGGCCCATCGGTCTTCCCCCTGGCACCCTCCTCCAAGAGCACCTCTGGGGGCACAGCGGCCCTGGGC

TGCCTGGTCAAGGACTACTTCCCCGAACCGGTGACGGTGTCGTGGAACTCAGGCGCCCTGACCAGCGGCGTGCA

CACCTTCCCGGCTGTCCTACAGTCCTCAGGACTCTACTCCCTCAGCAGCGTGGTGACCGTGCCCTCCAGCAGCT

TGGGCACCCAGACCTACATCTGCAACGTGAATCACAAGCCCAGCAACACCAAGGTGGACAAGAGAGTTGAGCCC

AAATCTTGTGACAAAACTCACACATGCCCACCGTGCCCAGCACCTGAAGCCGCGGGGGCACCGTCAGTCTTCCT

CTTCCCCCCAAAACCCAAGGACACCCTCATGATCTCCCGGACCCCTGAGGTCACATGCGTGGTGGTGGACGTGA

GCCACGAAGACCCTGAGGTCAAGTTCAACTGGTACGTGGACGGCGTGGAGGTGCATAATGCCAAGACAAAGCCG

CGGGAGGAGCAGTACAACAGCACGTACCGTGTGGTCAGCGTCCTCACCGTCCTGCACCAGGACTGGCTGAATGG

CAAGGAGTACAAGTGCGCGGTCTCCAACAAAGCCCTCCCAGCCCCCATCGAGAAAACCATCTCCAAAGCCAAAG

GGCAGCCCCGAGAACCACAGGTGTATACCCTGCCCCCATCCCGGGATGAGCTGACCAAGAACCAGGTCAGCCTG

ACCTGCCTGGTCAAAGGCTTCTATCCCAGCGACATCGCCGTGGAGTGGGAGAGCAATGGGCAGCCGGAGAACAA

CTACAAGACCACGCCTCCCGTGCTGGACTCCGACGGCTCCTTCTTCCTCTATAGCAAGCTCACCGTGGACAAGA

GCAGGTGGCAGCAGGGGAACGTCTTCTCATGCTCCGTGATGCATGAGGCTCTGCACAACCACTACACGCAGAAG

AGCTTAAGCCTGTCTCCGGGTGGCGGTGGAGGGTCCGGCGGTGGTGGATCCGAGGTGCAGCTGTTGGAGTCTGG

GGGAGGCTTGGTACAGCCTGGGGGGTCCCTGAGACTCTCCTGTGCAGCCTCTGGATTCTCCTTCAGTAGCGGGT

ACGACATGTGCTGGGTCCGCCAGGCTCCAGGGAAGGGGCTGGAGTGGATCGCATGCATTGCTGCTGGTAGTGCT

GGTATCACTTACGACGCGAACTGGGCGAAAGGCCGGTTCACCATCTCCAGAGACAATTCCAAGAACACGCTGTA

TCTGCAAATGAACAGCCTGAGAGCCGAGGACACGGCCGTATATTACTGTGCGAGATCGGCGTTTTCGTTCGACT

ACGCCATGGACCTCTGGGGCCAGGGAACCCTGGTCACCGTCTCGAGCGGTGGAGGCGGATCTGGCGGAGGTGGT

TCCGGCGGTGGCGGCTCCGGTGGAGGCGGCTCTGACATCCAGATGACCCAGTCTCCTTCCACCCTGTCTGCATC

TGTAGGAGACAGAGTCACCATCACTTGCCAGGCCAGTCAGAGCATTAGTTCCCACTTAAACTGGTATCAGCAGA

AACCAGGGAAAGCCCCTAAGCTCCTGATCTATAAGGCATCCACTCTGGCATCTGGGGTCCCATCAAGGTTCAGC

GGCAGTGGATCTGGGACAGAATTTACTCTCACCATCAGCAGCCTGCAGCCTGATGATTTTGCAACTTATTACTG

CCAACAGGGTTATAGTTGGGGTAATGTTGATAATGTTTTCGGCGGAGGGACCAAGGTGGAGATCAAA

SI-38E34 (21D4-LH-scFv x 284A10-L1H1-scFv x 420H5-Fab x PL221G5-H1L1-scFv) heavy chain aa

>SEQ ID: 38

AIQLTQSPSSLSASVGDRVTITCRASQGISSALAWYQQKPGKAPKLLIYDASSLESGVPSRFSGSGSGTDFTLT

ISSLQPEDFATYYCQQFNSYPFTFGPGTKVDIKGGGGSGGGGSGGGGSGGGGSEVQLVQSGAEVKKPGESLKIS

CKGSGYSFSSSWIGWVRQAPGKGLEWMGIIYPDDSDTRYSPSFQGQVTISADKSIRTAYLQWSSLKASDTAMYY

CARHVTMIWGVIIDFWGQGTLVTVSSGGGGSGGGGSDVVMTQSPSTLSASVGDRVTINCQASESISSWLAWYQQ

KPGKAPKLLIYEASKLASGVPSRFSGSGSGTEFTLTISSLQPDDFATYYCQGYFYFISRTYVNSFGGGTKVEIK

GGGGSGGGGSGGGGSGGGGSEVQLVESGGGLVQPGGSLRLSCAASGFTISTNAMSWVRQAPGKGLEWIGVITGR

DITYYASWAKGRFTISRDNSKNTLYLQMNSLRAEDTAVYYCARDGGSSAITSNNIWGQGTLVTVSSGGGGSGGG

GSQSLVESGGGLVQPGGSLRLSCAASGFSFSSNYWICWVRQAPGKGLEWIACIYVGSSGDTYYASSAKGRFTIS

RDNSKNTLYLQMNSLRAEDTAVYYCARDSSSYYMFNLWGQGTLVTVSSASTKGPSVFPLAPSSKSTSGGTAALG

CLVKDYFPEPVTVSWNSGALTSGVHTFPAVLQSSGLYSLSSVVTVPSSSLGTQTYICNVNHKPSNTKVDKRVEP

-continued

KSCDKTHTCPPCPAPEAAGAPSVFLFPPKPKDTLMISRTPEVTCVVVDVSHEDPEVKFNWYVDGVEVHNAKTKP

REEQYNSTYRVVSVLTVLHQDWLNGKEYKCAVSNKALPAPIEKTISKAKGQPREPQVYTLPPSRDELTKNQVSL

TCLVKGFYPSDIAVEWESNGQPENNYKTTPPVLDSDGSFFLYSKLTVDKSRWQQGNVFSCSVMHEALHNHYTQK

SLSLSPGGGGGSGGGGSEVQLLESGGGLVQPGGSLRLSCAASGFSFSSGYDMCWVRQAPGKGLEWIACIAAGSA

GITYDANWAKGRFTISRDNSKNTLYLQMNSLRAEDTAVYYCARSAFSFDYAMDLWGQGTLVTVSSGGGGSGGGG

SGGGGSGGGGSDIQMTQSPSTLSASVGDRVTITCQASQSISSHLNWYQQKPGKAPKLLIYKASTLASGVPSRFS

GSGSGTEFTLTISSLQPDDFATYYCQQGYSWGNVDNVFGGGTKVEIK

SI-38E34 (21D4-LH-scFv x 284A10-L1H1-scFv x 420H5-Fab x PL221G5-H1L1-scFv) light chain nt

>SEQ ID: 39

GCCCTTGTGATGACCCAGTCTCCTTCCACCCTGTCTGCATCTGTAGGAGACAGAGTCACCATCAATTGCCAGGC

CAGTGAGGACATTGATACCTATTTAGCCTGGTATCAGCAGAAACCAGGGAAAGCCCCTAAGCTCCTGATCTTTT

ATGCATCCGATCTGGCATCTGGGGTCCCATCAAGGTTCAGCGGCAGTGGATCTGGGACAGAATTCACTCTCACC

ATCAGCAGCCTGCAGCCTGATGATTTTGCAACTTATTACTGCCAAGGCGGTTACTATACTAGTAGTGCTGATAC

GAGGGGTGCTTTCGGCGGAGGGACCAAGGTGGAGATCAAACGTACGGTGGCTGCACCATCTGTCTTCATCTTCC

CGCCATCTGATGAGCAGTTGAAATCTGGAACTGCCTCTGTTGTGTGCCTGCTGAATAACTTCTATCCCAGAGAG

GCCAAAGTACAGTGGAAGGTGGATAACGCCCTCCAATCGGGTAACTCCCAGGAGAGTGTCACAGAGCAGGACAG

CAAGGACAGCACCTACAGCCTCAGCAGCACCCTGACGCTGAGCAAAGCAGACTACGAGAAACACAAAGTCTACG

CCTGCGAAGTCACCCATCAGGGCCTGAGCTCGCCCGTCACAAAGAGCTTCAACAGGGGAGAGTGT

SI-38E34 (21D4-LH-scFv x 284A10-L1H1-scFv x 420H5-Fab x PL221G5-H1L1-scFv) light chain aa

>SEQ ID: 40

ALVMTQSPSTLSASVGDRVTINCQASEDIDTYLAWYQQKPGKAPKLLIFYASDLASGVPSRFSGSGSGTEFTLT

ISSLQPDDFATYYCQGGYYTSSADTRGAFGGGTKVEIKRTVAAPSVFIFPPSDEQLKSGTASVVCLLNNFYPRE

AKVQWKVDNALQSGNSQESVTEQDSKDSTYSLSSTLTLSKADYEKHKVYACEVTHQGLSSPVTKSFNRGEC

---

What is claimed is:

1. A tetra-specific antibody monomer having a N-terminal and a C-terminal, comprising in tandem from the N-terminal to the C-terminal, a first scFv domain at the N-terminal comprising (i) 3 complementarity determining regions (CDRs) of SEQ ID NO: 26, and 3 CDRs of SEQ ID NO: 28; or (ii) 3 CDRs of SEQ ID NO: 30, and 3 CDRs of SEQ ID NO: 32, a second scFv domain comprising (i) 3 CDRs of SEQ ID NO: 2, and 3 CDRs of SEQ ID NO: 4: or (ii) 3 CDRs of SEQ ID NO: 6, and 3 CDRs of SEQ ID NO: 8, a Fab domain comprising (i) 3 CDRs of SEQ ID NO: 14, and 3 CDRs of SEQ ID NO: 16 ;

(ii) 3 CDRs of SEQ ID NO: 18, and 3 CDRs of SEQ ID NO: 20; or (iii) 3 CDRs of SEQ ID NO: 22, and 3 CDRs of SEQ ID NO: 24, a Fc domain, and a third scFv at the C-terminal comprising 3 CDRs of SEQ ID NO: 10, and 3 CDRs of SEQ ID NO: 12, wherein the first scFv domain, the second scFv domain, the Fab domain, and the third scFv domain each has a binding specificity against a different antigen, wherein the antigen is a tumor antigen, an immune signaling antigen, or a combination thereof, and wherein the first scFv domain, the second scFv domain, the Fab domain, and the third scFv domain have a binding specificity against CD19, CD3, 4-1BB, and PD-L1, respectively.

2. The tetra-specific antibody monomer of claim 1, wherein the Fc domain comprises a human IgG Fc domain.

3. The tetra-specific antibody monomer of claim 1, wherein the first scFv domain, the second scFv domain, or the third scFv domain comprises a gly-gly-gly-gly-ser $(G4S)_n$ (SEQ ID NO: 41) linker, wherein n is 2, 3 or 4.

4. The tetra-specific antibody monomer of claim 1, comprising the amino acid sequence SEQ ID NO: 38 and 40.

5. A tetra-specific antibody, comprising the tetra-specific antibody monomer of claim 1.

6. The tetra-specific antibody of claim 5, wherein the tetra-specific antibody is a dimer of the tetra-specific antibody monomers, wherein the tetra-specific antibody comprises the amino acid sequence SEQ ID NO:38 and 40.

7. A pharmaceutical composition, comprising a pharmaceutically acceptable carrier and the tetra-specific antibody of claim 5.

* * * * *

SEQUENCE LISTING

<160> NUMBER OF SEQ ID NOS: 41

<210> SEQ ID NO 1
<211> LENGTH: 360
<212> TYPE: DNA
<213> ORGANISM: Artificial Sequence
<220> FEATURE:
<223> OTHER INFORMATION: synthesized

<400> SEQUENCE: 1
gaggtgcagc tggtggagtc tgggggaggc ttggtccagc ctgggggtc cctgagactc 60 tcctgtgcag cctctggatt caccatcagt accaatgcaa tgagctgggt ccgccaggct 120
ccagggaagg ggctggagtg gatcggagtc attactggtc gtgatatcac atactacgcg 180
agctgggcga aaggcagatt caccatctcc agagacaatt ccaagaacac gctgtatctt 240
caaatgaaca gcctgagagc cgaggacacg gctgtgtatt actgtgcgcg cgacggtgga 300
tcatctgcta ttactagtaa caacatttgg ggccaaggaa ctctggtcac cgtttcttca 360

<210> SEQ ID NO 2
<211> LENGTH: 120
<212> TYPE: PRT
<213> ORGANISM: Artificial Sequence
<220> FEATURE:
<223> OTHER INFORMATION: synthesized

```
<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Ile Ser Thr Asn
            20                  25                  30

Ala Met Ser Trp Val Arg Gln Ala Pro Gly Lys Gly Leu Glu Trp Ile
        35                  40                  45

Gly Val Ile Thr Gly Arg Asp Ile Thr Tyr Tyr Ala Ser Trp Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Gly Gly Ser Ser Ala Ile Thr Ser Asn Asn Ile Trp Gly Gln
            100                 105                 110

Gly Thr Leu Val Thr Val Ser Ser
        115                 120


<210> SEQ ID NO 3
<211> LENGTH: 336
<212> TYPE: DNA
<213> ORGANISM: Artificial Sequence
<220> FEATURE:
<223> OTHER INFORMATION: synthesized

<400> SEQUENCE: 3

gacgtcgtga tgacccagtc tccttccacc ctgtctgcat ctgtaggaga cagagtcacc      60

atcaattgcc aagccagtga gagcattagc agttggttag cctggtatca gcagaaacca     120

gggaaagccc ctaagctcct gatctatgaa gcatccaaac tggcatctgg ggtcccatca     180

aggttcagcg gcagtggatc tgggacagag ttcactctca ccatcagcag cctgcagcct     240

gatgattttg caacttatta ctgccaaggc tatttttatt ttattagtcg tacttatgta     300

aattctttcg gcggagggac caaggtggag atcaaa                               336


<210> SEQ ID NO 4
<211> LENGTH: 112
<212> TYPE: PRT
<213> ORGANISM: Artificial Sequence
<220> FEATURE:
<223> OTHER INFORMATION: synthesized

<400> SEQUENCE: 4

Asp Val Val Met Thr Gln Ser Pro Ser Thr Leu Ser Ala Ser Val Gly
1               5                   10                  15

Asp Arg Val Thr Ile Asn Cys Gln Ala Ser Glu Ser Ile Ser Ser Trp
            20                  25                  30

Leu Ala Trp Tyr Gln Gln Lys Pro Gly Lys Ala Pro Lys Leu Leu Ile
        35                  40                  45

Tyr Glu Ala Ser Lys Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gly Tyr Phe Tyr Phe Ile Ser
                85                  90                  95

Arg Thr Tyr Val Asn Ser Phe Gly Gly Gly Thr Lys Val Glu Ile Lys
            100                 105                 110
```

<210> SEQ ID NO 5
<211> LENGTH: 375
<212> TYPE: DNA
<213> ORGANISM: Artificial Sequence
<220> FEATURE:
<223> OTHER INFORMATION: synthesized

<400> SEQUENCE: 5
caggtgcaat tggtggaaag cggaggggga ctggtgcagc ccgggggaag tctgaagctg 60
tcctgtgccg ccagcggctt taccttcaac aagtacgcca tgaattgggt ccgacaggcc 120
ccagggaaag gcctggaatg ggtggcacgg attcggtcca agtacaacaa ctacgccacc 180
tactacgctg actccgtgaa ggacagattc accatcagcc gggacgactc taagaacacc 240
gcctatctgc agatgaacaa cctgaaaacc gaggatacag ctgtgtacta ttgtgtgcgg 300
cacggcaact tcggcaactc ctacatctcc tactgggcct attggggaca gggaacactg 360
gtcaccgtgt ctagc 375

<210> SEQ ID NO 6
<211> LENGTH: 125
<212> TYPE: PRT
<213> ORGANISM: Artificial Sequence
<220> FEATURE:
<223> OTHER INFORMATION: synthesized

<400> SEQUENCE: 6

Gln Val Gln Leu Val Glu Ser Gly Gly Gly Leu Val Gln Pro Gly Gly
1 5 10 15

Ser Leu Lys Leu Ser Cys Ala Ala Ser Gly Phe Thr Phe Asn Lys Tyr
20 25 30

Ala Met Asn Trp Val Arg Gln Ala Pro Gly Lys Gly Leu Glu Trp Val
35 40 45

Ala Arg Ile Arg Ser Lys Tyr Asn Asn Tyr Ala Thr Tyr Tyr Ala Asp
50 55 60

Ser Val Lys Asp Arg Phe Thr Ile Ser Arg Asp Asp Ser Lys Asn Thr
65 70 75 80

Ala Tyr Leu Gln Met Asn Asn Leu Lys Thr Glu Asp Thr Ala Val Tyr
85 90 95

Tyr Cys Val Arg His Gly Asn Phe Gly Asn Ser Tyr Ile Ser Tyr Trp
100 105 110

Ala Tyr Trp Gly Gln Gly Thr Leu Val Thr Val Ser Ser
115 120 125

<210> SEQ ID NO 7
<211> LENGTH: 333
<212> TYPE: DNA
<213> ORGANISM: Artificial Sequence
<220> FEATURE:
<223> OTHER INFORMATION: synthesized

<400> SEQUENCE: 7
cagaccgtgg tcacccagga accttccctg accgtctccc caggcggcac cgtgaccctg 60
acctgtggct cctctaccgg cgctgtgacc tccggcaact accctaactg ggtgcagcag 120
aaacccggac aggctcctag aggcctgatc ggcggcacca agtttctggc ccctggcacc 180
cctgccagat tctccggctc cctgctggga ggcaaggccg ctctgaccct gtctggcgtg 240
cagcctgagg acgaggccga gtactactgt gtgctgtggt actccaacag atgggtgttc 300
ggaggcggca caaagctgac cgtgctgtcc tcg 333

<210> SEQ ID NO 8
<211> LENGTH: 111
<212> TYPE: PRT
<213> ORGANISM: Artificial Sequence
<220> FEATURE:
<223> OTHER INFORMATION: synthesized

<400> SEQUENCE: 8

```
Gln Thr Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

Asn Tyr Pro Asn Trp Val Gln Gln Lys Pro Gly Gln Ala Pro Arg Gly
        35                  40                  45

Leu Ile Gly Gly Thr Lys Phe Leu Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Val Leu Trp Tyr Ser Asn
                85                  90                  95

Arg Trp Val Phe Gly Gly Gly Thr Lys Leu Thr Val Leu Ser Ser
            100                 105                 110
```

<210> SEQ ID NO 9
<211> LENGTH: 366
<212> TYPE: DNA
<213> ORGANISM: Artificial Sequence
<220> FEATURE:
<223> OTHER INFORMATION: synthesized

<400> SEQUENCE: 9

```
gaggtgcagc tgttggagtc tgggggaggc ttggtacagc ctggggggtc cctgagactc     60

tcctgtgcag cctctggatt ctccttcagt agcgggtacg acatgtgctg ggtccgccag    120

gctccaggga aggggctgga gtggatcgca tgcattgctg ctggtagtgc tggtatcact    180

tacgacgcga actgggcgaa aggccggttc accatctcca gagacaattc caagaacacg    240

ctgtatctgc aaatgaacag cctgagagcc gaggacacgg ccgtatatta ctgtgcgaga    300

tcggcgtttt cgttcgacta cgccatggac ctctggggcc agggaaccct ggtcaccgtc    360

tcgagc                                                               366
```

<210> SEQ ID NO 10
<211> LENGTH: 122
<212> TYPE: PRT
<213> ORGANISM: Artificial Sequence
<220> FEATURE:
<223> OTHER INFORMATION: synthesized

<400> SEQUENCE: 10

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Ser Phe Ser Ser Gly
            20                  25                  30

Tyr Asp Met Cys Trp Val Arg Gln Ala Pro Gly Lys Gly Leu Glu Trp
        35                  40                  45

Ile Ala Cys Ile Ala Ala Gly Ser Ala Gly Ile Thr Tyr Asp Ala Asn
    50                  55                  60
```

```
Trp Ala Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Ser Ala Phe Ser Phe Asp Tyr Ala Met Asp Leu Trp
            100                 105                 110

Gly Gln Gly Thr Leu Val Thr Val Ser Ser
        115                 120


<210> SEQ ID NO 11
<211> LENGTH: 330
<212> TYPE: DNA
<213> ORGANISM: Artificial Sequence
<220> FEATURE:
<223> OTHER INFORMATION: synthesized

<400> SEQUENCE: 11

gacatccaga tgacccagtc tccttccacc ctgtctgcat ctgtaggaga cagagtcacc      60

atcacttgcc aggccagtca gagcattagt tcccacttaa actggtatca gcagaaacca     120

gggaaagccc ctaagctcct gatctataag gcatccactc tggcatctgg ggtcccatca     180

aggttcagcg gcagtggatc tgggacagaa tttactctca ccatcagcag cctgcagcct     240

gatgattttg caacttatta ctgccaacag ggttatagtt ggggtaatgt tgataatgtt     300

ttcggcggag ggaccaaggt ggagatcaaa                                      330


<210> SEQ ID NO 12
<211> LENGTH: 110
<212> TYPE: PRT
<213> ORGANISM: Artificial Sequence
<220> FEATURE:
<223> OTHER INFORMATION: synthesized

<400> SEQUENCE: 12

Asp Ile Gln Met Thr Gln Ser Pro Ser Thr Leu Ser Ala Ser Val Gly
1               5                   10                  15

Asp Arg Val Thr Ile Thr Cys Gln Ala Ser Gln Ser Ile Ser Ser His
            20                  25                  30

Leu Asn Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Gly Tyr Ser Trp Gly Asn
                85                  90                  95

Val Asp Asn Val Phe Gly Gly Gly Thr Lys Val Glu Ile Lys
            100                 105                 110


<210> SEQ ID NO 13
<211> LENGTH: 360
<212> TYPE: DNA
<213> ORGANISM: Artificial Sequence
<220> FEATURE:
<223> OTHER INFORMATION: synthesized

<400> SEQUENCE: 13

cagtcgctgg tggagtctgg gggaggcttg gtacagcctg gggggtccct gagactctcc      60

tgtgcagcct ctggattctc cttcagtagc aactactgga tatgctgggt ccgccaggct     120
```

```
ccagggaagg ggctggagtg gatcgcatgc atttatgttg gtagtagtgg tgacacttac    180

tacgcgagct ccgcgaaagg ccggttcacc atctccagag acaattccaa gaacacgctg    240

tatctgcaaa tgaacagcct gagagccgag gacacggccg tatattactg tgcgagagat    300

agtagtagtt attatatgtt taacttgtgg ggccagggaa ccctggtcac cgtctcgagc    360


<210> SEQ ID NO 14
<211> LENGTH: 120
<212> TYPE: PRT
<213> ORGANISM: Artificial Sequence
<220> FEATURE:
<223> OTHER INFORMATION: synthesized

<400> SEQUENCE: 14

Gln Ser Leu Val Glu Ser Gly Gly Gly Leu Val Gln Pro Gly Gly Ser
1               5                   10                  15

Leu Arg Leu Ser Cys Ala Ala Ser Gly Phe Ser Phe Ser Ser Asn Tyr
            20                  25                  30

Trp Ile Cys Trp Val Arg Gln Ala Pro Gly Lys Gly Leu Glu Trp Ile
        35                  40                  45

Ala Cys Ile Tyr Val Gly Ser Ser Gly Asp Thr Tyr Tyr Ala Ser Ser
    50                  55                  60

Ala Lys Gly Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Asp Ser Ser Ser Tyr Tyr Met Phe Asn Leu Trp Gly Gln
            100                 105                 110

Gly Thr Leu Val Thr Val Ser Ser
        115                 120


<210> SEQ ID NO 15
<211> LENGTH: 336
<212> TYPE: DNA
<213> ORGANISM: Artificial Sequence
<220> FEATURE:
<223> OTHER INFORMATION: synthesized

<400> SEQUENCE: 15

gcccttgtga tgacccagtc tccttccacc ctgtctgcat ctgtaggaga cagagtcacc     60

atcaattgcc aggccagtga ggacattgat acctatttag cctggtatca gcagaaacca    120

gggaaagccc ctaagctcct gatcttttat gcatccgatc tggcatctgg ggtcccatca    180

aggttcagcg gcagtggatc tgggacagaa ttcactctca ccatcagcag cctgcagcct    240

gatgattttg caacttatta ctgccaaggc ggttactata ctagtagtgc tgatacgagg    300

ggtgctttcg gcggagggac caaggtggag atcaaa                              336


<210> SEQ ID NO 16
<211> LENGTH: 112
<212> TYPE: PRT
<213> ORGANISM: Artificial Sequence
<220> FEATURE:
<223> OTHER INFORMATION: synthesized

<400> SEQUENCE: 16

Ala Leu Val Met Thr Gln Ser Pro Ser Thr Leu Ser Ala Ser Val Gly
1               5                   10                  15
```

```
Asp Arg Val Thr Ile Asn Cys Gln Ala Ser Glu Asp Ile Asp Thr Tyr
            20                  25                  30

Leu Ala Trp Tyr Gln Gln Lys Pro Gly Lys Ala Pro Lys Leu Leu Ile
        35                  40                  45

Phe Tyr Ala Ser Asp Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gly Gly Tyr Tyr Thr Ser Ser
                85                  90                  95

Ala Asp Thr Arg Gly Ala Phe Gly Gly Gly Thr Lys Val Glu Ile Lys
            100                 105                 110
```

<210> SEQ ID NO 17
<211> LENGTH: 345
<212> TYPE: DNA
<213> ORGANISM: Artificial Sequence
<220> FEATURE:
<223> OTHER INFORMATION: synthesized

<400> SEQUENCE: 17

```
cggtcgctgg tggagtctgg gggaggcttg gtccagcctg gggggtccct gagactctcc     60

tgtacagcct ctggattcac catcagtagc taccacatgc agtgggtccg ccaggctcca    120

gggaaggggc tggagtacat cggaaccatt agtagtggtg gtaatgtata ctacgcgagc    180

tccgcgagag gcagattcac catctccaga ccctcgtcca agaacacggt ggatcttcaa    240

atgaacagcc tgagagccga ggacacggct gtgtattact gtgcgagaga ctctggttat    300

agtgatccta tgtggggcca gggaaccctg gtcaccgtct cgagc                    345
```

<210> SEQ ID NO 18
<211> LENGTH: 115
<212> TYPE: PRT
<213> ORGANISM: Artificial Sequence
<220> FEATURE:
<223> OTHER INFORMATION: synthesized

<400> SEQUENCE: 18

```
Arg Ser Leu Val Glu Ser Gly Gly Gly Leu Val Gln Pro Gly Gly Ser
1               5                   10                  15

Leu Arg Leu Ser Cys Thr Ala Ser Gly Phe Thr Ile Ser Ser Tyr His
            20                  25                  30

Met Gln Trp Val Arg Gln Ala Pro Gly Lys Gly Leu Glu Tyr Ile Gly
        35                  40                  45

Thr Ile Ser Ser Gly Gly Asn Val Tyr Tyr Ala Ser Ser Ala Arg Gly
    50                  55                  60

Arg Phe Thr Ile Ser Arg Pro Ser Ser Lys Asn Thr Val Asp Leu Gln
65                  70                  75                  80

Met Asn Ser Leu Arg Ala Glu Asp Thr Ala Val Tyr Tyr Cys Ala Arg
                85                  90                  95

Asp Ser Gly Tyr Ser Asp Pro Met Trp Gly Gln Gly Thr Leu Val Thr
            100                 105                 110

Val Ser Ser
        115
```

<210> SEQ ID NO 19
<211> LENGTH: 333
<212> TYPE: DNA

<213> ORGANISM: Artificial Sequence
<220> FEATURE:
<223> OTHER INFORMATION: synthesized

<400> SEQUENCE: 19

```
gacgttgtga tgacccagtc tccatcttcc gtgtctgcat ctgtaggaga cagagtcacc     60

atcacctgtc aggccagtca gaacattagg acttacttat cctggtatca gcagaaacca    120

gggaaagccc ctaagctcct gatctatgct gcagccaatc tggcatctgg ggtcccatca    180

aggttcagcg gcagtggatc tgggacagat ttcactctca ccatcagcga cctggagcct    240

ggcgatgctg caacttacta ttgtcagtct acctatcttg gtactgatta tgttggcggt    300

gctttcggcg gagggaccaa ggtggagatc aaa                                 333
```

<210> SEQ ID NO 20
<211> LENGTH: 111
<212> TYPE: PRT
<213> ORGANISM: Artificial Sequence
<220> FEATURE:
<223> OTHER INFORMATION: synthesized

<400> SEQUENCE: 20

```
Asp Val Val Met Thr Gln Ser Pro Ser Ser Val Ser Ala Ser Val Gly
1               5                   10                  15

Asp Arg Val Thr Ile Thr Cys Gln Ala Ser Gln Asn Ile Arg Thr Tyr
            20                  25                  30

Leu Ser Trp Tyr Gln Gln Lys Pro Gly Lys Ala Pro Lys Leu Leu Ile
        35                  40                  45

Tyr Ala Ala Ala Asn Leu Ala Ser Gly Val Pro Ser Arg Phe Ser Gly
    50                  55                  60

Ser Gly Ser Gly Thr Asp Phe Thr Leu Thr Ile Ser Asp Leu Glu Pro
65                  70                  75                  80

Gly Asp Ala Ala Thr Tyr Tyr Cys Gln Ser Thr Tyr Leu Gly Thr Asp
                85                  90                  95

Tyr Val Gly Gly Ala Phe Gly Gly Gly Thr Lys Val Glu Ile Lys
            100                 105                 110
```

<210> SEQ ID NO 21
<211> LENGTH: 345
<212> TYPE: DNA
<213> ORGANISM: Artificial Sequence
<220> FEATURE:
<223> OTHER INFORMATION: synthesized

<400> SEQUENCE: 21

```
gaggtgcagc tgttggagtc tgggggaggc ttggtacagc ctggggggtc cctgagactc     60

tcctgtgcag cctctggaat cgacttcagt aggagatact acatgtgctg ggtccgccag    120

gctccaggga aggggctgga gtggatcgca tgcatatata ctggtagccg cgatactcct    180

cactacgcga gctccgcgaa aggccggttc accatctcca gagacaattc caagaacacg    240

ctgtatctgc aaatgaacag cctgagagcc gaggacacgg ccgtatatta ctgtgcgaga    300

gaaggtagcc tgtggggcca gggaaccctg gtcaccgtct cgagc                    345
```

<210> SEQ ID NO 22
<211> LENGTH: 115
<212> TYPE: PRT
<213> ORGANISM: Artificial Sequence
<220> FEATURE:
<223> OTHER INFORMATION: synthesized

```
<400> SEQUENCE: 22

Glu Val Gln Leu Leu Glu Ser Gly Gly Gly Leu Val Gln Pro Gly Gly
1               5                   10                  15

Ser Leu Arg Leu Ser Cys Ala Ala Ser Gly Ile Asp Phe Ser Arg Arg
            20                  25                  30

Tyr Tyr Met Cys Trp Val Arg Gln Ala Pro Gly Lys Gly Leu Glu Trp
        35                  40                  45

Ile Ala Cys Ile Tyr Thr Gly Ser Arg Asp Thr Pro His Tyr Ala Ser
    50                  55                  60

Ser Ala Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Ala Arg Glu Gly Ser Leu Trp Gly Gln Gly Thr Leu Val Thr
            100                 105                 110

Val Ser Ser
        115


<210> SEQ ID NO 23
<211> LENGTH: 333
<212> TYPE: DNA
<213> ORGANISM: Artificial Sequence
<220> FEATURE:
<223> OTHER INFORMATION: synthesized

<400> SEQUENCE: 23

gacatccaga tgacccagtc tccttccacc ctgtctgcat ctgtaggaga cagagtcacc     60

atcacttgcc agtccagtca gagtgtttat agtaactggt tctcctggta tcagcagaaa    120

ccagggaaag cccctaagct cctgatctat tctgcatcca ctctggcatc tggggtccca    180

tcaaggttca gcggcagtgg atctgggaca gaattcactc tcaccatcag cagcctgcag    240

cctgatgatt ttgcaactta ttactgcgca ggcggttaca atactgttat tgatactttt    300

gctttcggcg gagggaccaa ggtggagatc aaa                                 333


<210> SEQ ID NO 24
<211> LENGTH: 111
<212> TYPE: PRT
<213> ORGANISM: Artificial Sequence
<220> FEATURE:
<223> OTHER INFORMATION: synthesized

<400> SEQUENCE: 24

Asp Ile Gln Met Thr Gln Ser Pro Ser Thr Leu Ser Ala Ser Val Gly
1               5                   10                  15

Asp Arg Val Thr Ile Thr Cys Gln Ser Ser Gln Ser Val Tyr Ser Asn
            20                  25                  30

Trp Phe Ser Trp Tyr Gln Gln Lys Pro Gly Lys Ala Pro Lys Leu Leu
        35                  40                  45

Ile Tyr Ser Ala Ser Thr Leu Ala Ser Gly Val Pro Ser Arg Phe Ser
    50                  55                  60

Gly Ser Gly Ser Gly Thr Glu Phe Thr Leu Thr Ile Ser Ser Leu Gln
65                  70                  75                  80

Pro Asp Asp Phe Ala Thr Tyr Tyr Cys Ala Gly Gly Tyr Asn Thr Val
                85                  90                  95

Ile Asp Thr Phe Ala Phe Gly Gly Gly Thr Lys Val Glu Ile Lys
            100                 105                 110
```

<210> SEQ ID NO 25
<211> LENGTH: 363
<212> TYPE: DNA
<213> ORGANISM: Artificial Sequence
<220> FEATURE:
<223> OTHER INFORMATION: synthesized

<400> SEQUENCE: 25

```
gaggtgcagc tggtgcagtc tggagcagag gtgaagaaac caggagagtc tctgaagatc     60

tcctgtaagg gttctggata cagctttagc agttcatgga tcggctgggt gcgccaggca    120

cctgggaaag gcctggaatg gatggggatc atctatcctg atgactctga taccagatac    180

agtccatcct tccaaggcca ggtcaccatc tcagccgaca agtccatcag gactgcctac    240

ctgcagtgga gtagcctgaa ggcctcggac accgctatgt attactgtgc gagacatgtt    300

actatgattt ggggagttat tattgacttc tggggccagg gaaccctggt caccgtctcc    360

tca                                                                  363
```

<210> SEQ ID NO 26
<211> LENGTH: 121
<212> TYPE: PRT
<213> ORGANISM: Artificial Sequence
<220> FEATURE:
<223> OTHER INFORMATION: synthesized

<400> SEQUENCE: 26

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ser Ser Ser
            20                  25                  30

Trp Ile Gly Trp Val Arg Gln Ala Pro Gly Lys Gly Leu Glu Trp Met
        35                  40                  45

Gly Ile Ile Tyr Pro Asp Asp Ser Asp Thr Arg Tyr Ser Pro Ser Phe
    50                  55                  60

Gln Gly Gln Val Thr Ile Ser Ala Asp Lys Ser Ile Arg Thr Ala Tyr
65                  70                  75                  80

Leu Gln Trp Ser Ser Leu Lys Ala Ser Asp Thr Ala Met Tyr Tyr Cys
                85                  90                  95

Ala Arg His Val Thr Met Ile Trp Gly Val Ile Ile Asp Phe Trp Gly
            100                 105                 110

Gln Gly Thr Leu Val Thr Val Ser Ser
        115                 120
```

<210> SEQ ID NO 27
<211> LENGTH: 321
<212> TYPE: DNA
<213> ORGANISM: Artificial Sequence
<220> FEATURE:
<223> OTHER INFORMATION: synthesized

<400> SEQUENCE: 27

```
gccatccagt tgacccagtc tccatcctcc ctgtctgcat ctgtaggaga cagagtcacc     60

atcacttgcc gggcaagtca gggcattagc agtgctttag cctggtatca gcagaaacca    120

gggaaagctc ctaagctcct gatctatgat gcctccagtt tggaaagtgg ggtcccatca    180

aggttcagcg gcagtggatc tgggacagat ttcactctca ccatcagcag cctgcagcct    240

gaagattttg caacttatta ctgtcaacag tttaatagtt acccattcac tttcggccct    300

gggaccaaag tggatatcaa a                                              321
```

<210> SEQ ID NO 28
<211> LENGTH: 107
<212> TYPE: PRT
<213> ORGANISM: Artificial Sequence
<220> FEATURE:
<223> OTHER INFORMATION: synthesized

<400> SEQUENCE: 28

```
Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Phe
                85                  90                  95

Thr Phe Gly Pro Gly Thr Lys Val Asp Ile Lys
            100                 105
```

<210> SEQ ID NO 29
<211> LENGTH: 372
<212> TYPE: DNA
<213> ORGANISM: Artificial Sequence
<220> FEATURE:
<223> OTHER INFORMATION: synthesized

<400> SEQUENCE: 29

```
caggtccaac tccagcagtc tggggctgag ctggtgaggc ctgggtcctc agtgaagatt      60

tcctgcaagg cttctggcta tgccttcagt agctactgga tgaactgggt gaagcagagg     120

cctggacagg gtcttgagtg gattggacag atttggcctg gagatggtga tactaactac     180

aatggaaagt tcaaggggaa agccactctg actgcagacg aatcctccag cacagcctac     240

atgcaactca gcagcctagc atctgaggac tctgcggtct atttctgtgc aagacgggag     300

actacgacgg taggccgtta ttactatgct atggactact ggggccaagg gaccacggtc     360

accgtctcct cc                                                         372
```

<210> SEQ ID NO 30
<211> LENGTH: 124
<212> TYPE: PRT
<213> ORGANISM: Artificial Sequence
<220> FEATURE:
<223> OTHER INFORMATION: synthesized

<400> SEQUENCE: 30

```
Gln Val Gln Leu Gln Gln Ser Gly Ala Glu Leu Val Arg Pro Gly Ser
1               5                   10                  15

Ser Val Lys Ile Ser Cys Lys Ala Ser Gly Tyr Ala Phe Ser Ser Tyr
            20                  25                  30

Trp Met Asn Trp Val Lys Gln Arg Pro Gly Gln Gly Leu Glu Trp Ile
        35                  40                  45

Gly Gln Ile Trp Pro Gly Asp Gly Asp Thr Asn Tyr Asn Gly Lys Phe
    50                  55                  60
```

```
Lys Gly Lys Ala Thr Leu Thr Ala Asp Glu Ser Ser Ser Thr Ala Tyr
65                  70                  75                  80

Met Gln Leu Ser Ser Leu Ala Ser Glu Asp Ser Ala Val Tyr Phe Cys
                85                  90                  95

Ala Arg Arg Glu Thr Thr Thr Val Gly Arg Tyr Tyr Tyr Ala Met Asp
            100                 105                 110

Tyr Trp Gly Gln Gly Thr Thr Val Thr Val Ser Ser
        115                 120


<210> SEQ ID NO 31
<211> LENGTH: 333
<212> TYPE: DNA
<213> ORGANISM: Artificial Sequence
<220> FEATURE:
<223> OTHER INFORMATION: synthesized

<400> SEQUENCE: 31

gatatccagc tgacccagtc tccagcttct ttggctgtgt ctctagggca gagggccacc     60

atctcctgca aggccagcca aagtgttgat tatgatggtg tgagttactt gaactggtat    120

caacagattc caggacagcc acccaaactc ctcatctatg atgcttccaa tctagtttct    180

gggatcccac ccaggtttag tggcagtggg tctgggacag acttcaccct caacatccat    240

cctgtggaga aggtggatgc tgcaacctat cactgtcagc aaagtactga ggatccgtgg    300

acgttcggtg gagggaccaa gctcgagatt aaa                                 333


<210> SEQ ID NO 32
<211> LENGTH: 111
<212> TYPE: PRT
<213> ORGANISM: Artificial Sequence
<220> FEATURE:
<223> OTHER INFORMATION: synthesized

<400> SEQUENCE: 32

Asp Ile Gln Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Val Ser Tyr Leu Asn Trp Tyr Gln Gln Ile Pro Gly Gln Pro Pro
        35                  40                  45

Lys Leu Leu Ile Tyr Asp Ala Ser Asn Leu Val Ser Gly Ile Pro Pro
    50                  55                  60

Arg Phe Ser Gly Ser Gly Ser Gly Thr Asp Phe Thr Leu Asn Ile His
65                  70                  75                  80

Pro Val Glu Lys Val Asp Ala Ala Thr Tyr His Cys Gln Gln Ser Thr
                85                  90                  95

Glu Asp Pro Trp Thr Phe Gly Gly Gly Thr Lys Leu Glu Ile Lys
            100                 105                 110


<210> SEQ ID NO 33
<211> LENGTH: 987
<212> TYPE: DNA
<213> ORGANISM: Artificial Sequence
<220> FEATURE:
<223> OTHER INFORMATION: synthesized

<400> SEQUENCE: 33

gctagcacca agggcccatc ggtcttcccc ctggcaccct cctccaagag cacctctggg     60

ggcacagcgg ccctgggctg cctggtcaag gactacttcc ccgaaccggt gacggtgtcg    120
```

```
tggaactcag gcgccctgac cagcggcgtg cacaccttcc cggctgtcct acagtcctca    180

ggactctact ccctcagcag cgtggtgacc gtgccctcca gcagcttggg cacccagacc    240

tacatctgca acgtgaatca caagcccagc aacaccaagg tggacaagag agttgagccc    300

aaatcttgtg acaaaactca cacatgccca ccgtgcccag cacctgaagc cgcgggggca    360

ccgtcagtct tcctcttccc cccaaaaccc aaggacaccc tcatgatctc ccggacccct    420

gaggtcacat gcgtggtggt ggacgtgagc cacgaagacc ctgaggtcaa gttcaactgg    480

tacgtggacg gcgtggaggt gcataatgcc aagacaaagc cgcgggagga gcagtacaac    540

agcacgtacc gtgtggtcag cgtcctcacc gtcctgcacc aggactggct gaatggcaag    600

gagtacaagt gcgcggtctc caacaaagcc ctcccagccc ccatcgagaa aaccatctcc    660

aaagccaaag ggcagccccg agaaccacag gtgtacaccc tgcccccatc ccgggatgag    720

ctgaccaaga accaggtcag cctgacctgc ctggtcaaag gcttctatcc cagcgacatc    780

gccgtggagt gggagagcaa tgggcagccg gagaacaact acaagaccac gcctcccgtg    840

ctggactccg acggctcctt cttcctctat agcaagctca ccgtggacaa gagcaggtgg    900

cagcagggga acgtcttctc atgctccgtg atgcatgagg ctctgcacaa ccactacacg    960

cagaagagcc tctccctgtc tccgggt                                        987
```

```
<210> SEQ ID NO 34
<211> LENGTH: 329
<212> TYPE: PRT
<213> ORGANISM: Artificial Sequence
<220> FEATURE:
<223> OTHER INFORMATION: synthesized

<400> SEQUENCE: 34

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Ala Ala Gly Ala Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Ala Val Ser Asn
        195                 200                 205
```

```
Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325


<210> SEQ ID NO 35
<211> LENGTH: 321
<212> TYPE: DNA
<213> ORGANISM: Artificial Sequence
<220> FEATURE:
<223> OTHER INFORMATION: synthesized

<400> SEQUENCE: 35

cgtacggtgg ctgcaccatc tgtcttcatc ttcccgccat ctgatgagca gttgaaatct     60

ggaactgcct ctgttgtgtg cctgctgaat aacttctatc ccagagaggc caaagtacag    120

tggaaggtgg ataacgccct ccaatcgggt aactcccagg agagtgtcac agagcaggac    180

agcaaggaca gcacctacag cctcagcagc accctgacgc tgagcaaagc agactacgag    240

aaacacaaag tctacgcctg cgaagtcacc catcagggcc tgagctcgcc cgtcacaaag    300

agcttcaaca ggggagagtg t                                              321


<210> SEQ ID NO 36
<211> LENGTH: 107
<212> TYPE: PRT
<213> ORGANISM: Artificial Sequence
<220> FEATURE:
<223> OTHER INFORMATION: synthesized

<400> SEQUENCE: 36

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 37
<211> LENGTH: 3693
<212> TYPE: DNA
<213> ORGANISM: Artificial Sequence
<220> FEATURE:
<223> OTHER INFORMATION: synthesized

<400> SEQUENCE: 37
gccatccagt tgacccagtc tccatcctcc ctgtctgcat ctgtaggaga cagagtcacc 60
atcacttgcc gggcaagtca gggcattagc agtgctttag cctggtatca gcagaaacca 120
gggaaagctc ctaagctcct gatctatgat gcctccagtt tggaaagtgg ggtcccatca 180
aggttcagcg gcagtggatc tgggacagat ttcactctca ccatcagcag cctgcagcct 240
gaagattttg caacttatta ctgtcaacag tttaatagtt acccattcac tttcggccct 300
gggaccaaag tggatatcaa aggcggtggc ggtagtgggg gaggcggttc tggcggcgga 360
gggtccggcg gtggaggatc agaggtgcag ctggtgcagt ctggagcaga ggtgaagaaa 420
ccaggagagt ctctgaagat ctcctgtaag ggttctggat acagctttag cagttcatgg 480
atcggctggg tgcgccaggc acctgggaaa ggcctggaat ggatggggat catctatcct 540
gatgactctg ataccagata cagtccatcc ttccaaggcc aggtcaccat ctcagccgac 600
aagtccatca ggactgccta cctgcagtgg agtagcctga aggcctcgga caccgctatg 660
tattactgtg cgagacatgt tactatgatt tggggagtta ttattgactt ctggggccag 720
ggaaccctgg tcaccgtctc ctcaggcggt ggagggtccg gcggtggtgg atccgacgtc 780
gtgatgaccc agtctccttc caccctgtct gcatctgtag gagacagagt caccatcaat 840
tgccaagcca gtgagagcat tagcagttgg ttagcctggt atcagcagaa accagggaaa 900
gcccctaagc tcctgatcta tgaagcatcc aaactggcat ctggggtccc atcaaggttc 960
agcggcagtg gatctgggac agagttcact ctcaccatca gcagcctgca gcctgatgat 1020
tttgcaactt attactgcca aggctatttt tattttatta gtcgtactta tgtaaattct 1080
ttcggcggag ggaccaaggt ggagatcaaa ggcggtggcg gtagtggggg aggcggttct 1140
ggcggcggag ggtccggcgg tggaggatca gaggtgcagc tggtggagtc tgggggaggc 1200
ttggtccagc ctggggggtc cctgagactc tcctgtgcag cctctggatt caccatcagt 1260
accaatgcaa tgagctgggt ccgccaggct ccagggaagg ggctggagtg gatcggagtc 1320
attactggtc gtgatatcac atactacgcg agctgggcga aaggcagatt caccatctcc 1380
agagacaatt ccaagaacac gctgtatctt caaatgaaca gcctgagagc cgaggacacg 1440
gctgtgtatt actgtgcgcg cgacggtgga tcatctgcta ttactagtaa caacatttgg 1500
ggccaaggaa ctctggtcac cgtttcttca ggcggtggag ggtccggagg tggtggctcc 1560
cagtcgctgg tggagtctgg gggaggcttg gtacagcctg gggggtccct gagactctcc 1620
tgtgcagcct ctggattctc cttcagtagc aactactgga tatgctgggt ccgccaggct 1680
ccagggaagg ggctggagtg gatcgcatgc atttatgttg gtagtagtgg tgacacttac 1740
tacgcgagct ccgcgaaagg ccggttcacc atctccagag acaattccaa gaacacgctg 1800
tatctgcaaa tgaacagcct gagagccgag gacacggccg tatattactg tgcgagagat 1860
agtagtagtt attatatgtt taacttgtgg ggccagggaa ccctggtcac cgtctcgagc 1920
gctagcacca agggcccatc ggtcttcccc ctggcaccct cctccaagag cacctctggg 1980
ggcacagcgg ccctgggctg cctggtcaag gactacttcc ccgaaccggt gacggtgtcg 2040
tggaactcag gcgccctgac cagcggcgtg cacaccttcc cggctgtcct acagtcctca 2100

```
ggactctact ccctcagcag cgtggtgacc gtgccctcca gcagcttggg cacccagacc   2160
tacatctgca acgtgaatca caagcccagc aacaccaagg tggacaagag agttgagccc   2220
aaatcttgtg acaaaactca cacatgccca ccgtgcccag cacctgaagc cgcgggggca   2280
ccgtcagtct tcctcttccc cccaaaaccc aaggacaccc tcatgatctc ccggacccct   2340
gaggtcacat gcgtggtggt ggacgtgagc cacgaagacc ctgaggtcaa gttcaactgg   2400
tacgtggacg gcgtggaggt gcataatgcc aagacaaagc cgcgggagga gcagtacaac   2460
agcacgtacc gtgtggtcag cgtcctcacc gtcctgcacc aggactggct gaatggcaag   2520
gagtacaagt gcgcggtctc caacaaagcc ctcccagccc ccatcgagaa aaccatctcc   2580
aaagccaaag ggcagccccg agaaccacag gtgtataccc tgcccccatc ccgggatgag   2640
ctgaccaaga accaggtcag cctgacctgc ctggtcaaag gcttctatcc cagcgacatc   2700
gccgtggagt gggagagcaa tgggcagccg gagaacaact acaagaccac gcctcccgtg   2760
ctggactccg acggctcctt cttcctctat agcaagctca ccgtggacaa gagcaggtgg   2820
cagcagggga acgtcttctc atgctccgtg atgcatgagg ctctgcacaa ccactacacg   2880
cagaagagct taagcctgtc tccgggtggc ggtggagggt ccggcggtgg tggatccgag   2940
gtgcagctgt tggagtctgg gggaggcttg gtacagcctg gggggtccct gagactctcc   3000
tgtgcagcct ctggattctc cttcagtagc gggtacgaca tgtgctgggt ccgccaggct   3060
ccagggaagg ggctggagtg gatcgcatgc attgctgctg gtagtgctgg tatcacttac   3120
gacgcgaact gggcgaaagg ccggttcacc atctccagag acaattccaa gaacacgctg   3180
tatctgcaaa tgaacagcct gagagccgag gacacggccg tatattactg tgcgagatcg   3240
gcgttttcgt tcgactacgc catggacctc tggggccagg gaaccctggt caccgtctcg   3300
agcggtggag gcggatctgg cggaggtggt tccggcggtg gcggctccgg tggaggcggc   3360
tctgacatcc agatgaccca gtctccttcc accctgtctg catctgtagg agacagagtc   3420
accatcactt gccaggccag tcagagcatt agttcccact taaactggta tcagcagaaa   3480
ccagggaaag cccctaagct cctgatctat aaggcatcca ctctggcatc tggggtccca   3540
tcaaggttca gcggcagtgg atctgggaca gaatttactc tcaccatcag cagcctgcag   3600
cctgatgatt ttgcaactta ttactgccaa cagggttata gttggggtaa tgttgataat   3660
gttttcggcg gagggaccaa ggtggagatc aaa                                 3693
```

```
<210> SEQ ID NO 38
<211> LENGTH: 1231
<212> TYPE: PRT
<213> ORGANISM: Artificial Sequence
<220> FEATURE:
<223> OTHER INFORMATION: synthesized

<400> SEQUENCE: 38

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln Phe Asn Ser Tyr Pro Phe
                85                  90                  95

Thr Phe Gly Pro Gly Thr Lys Val Asp Ile Lys Gly Gly Gly Gly Ser
            100                 105                 110

Gly Gly Gly Gly Ser Gly Gly Gly Gly Ser Gly Gly Gly Gly Ser Glu
        115                 120                 125

Val Gln Leu Val Gln Ser Gly Ala Glu Val Lys Lys Pro Gly Glu Ser
    130                 135                 140

Leu Lys Ile Ser Cys Lys Gly Ser Gly Tyr Ser Phe Ser Ser Ser Trp
145                 150                 155                 160

Ile Gly Trp Val Arg Gln Ala Pro Gly Lys Gly Leu Glu Trp Met Gly
                165                 170                 175

Ile Ile Tyr Pro Asp Asp Ser Asp Thr Arg Tyr Ser Pro Ser Phe Gln
            180                 185                 190

Gly Gln Val Thr Ile Ser Ala Asp Lys Ser Ile Arg Thr Ala Tyr Leu
        195                 200                 205

Gln Trp Ser Ser Leu Lys Ala Ser Asp Thr Ala Met Tyr Tyr Cys Ala
    210                 215                 220

Arg His Val Thr Met Ile Trp Gly Val Ile Ile Asp Phe Trp Gly Gln
225                 230                 235                 240

Gly Thr Leu Val Thr Val Ser Ser Gly Gly Gly Gly Ser Gly Gly Gly
                245                 250                 255

Gly Ser Asp Val Val Met Thr Gln Ser Pro Ser Thr Leu Ser Ala Ser
            260                 265                 270

Val Gly Asp Arg Val Thr Ile Asn Cys Gln Ala Ser Glu Ser Ile Ser
        275                 280                 285

Ser Trp Leu Ala Trp Tyr Gln Gln Lys Pro Gly Lys Ala Pro Lys Leu
    290                 295                 300

Leu Ile Tyr Glu Ala Ser Lys Leu Ala Ser Gly Val Pro Ser Arg Phe
305                 310                 315                 320

Ser Gly Ser Gly Ser Gly Thr Glu Phe Thr Leu Thr Ile Ser Ser Leu
                325                 330                 335

Gln Pro Asp Asp Phe Ala Thr Tyr Tyr Cys Gln Gly Tyr Phe Tyr Phe
            340                 345                 350

Ile Ser Arg Thr Tyr Val Asn Ser Phe Gly Gly Gly Thr Lys Val Glu
        355                 360                 365

Ile Lys Gly Gly Gly Gly Ser Gly Gly Gly Gly Ser Gly Gly Gly Gly
    370                 375                 380

Ser Gly Gly Gly Gly Ser Glu Val Gln Leu Val Glu Ser Gly Gly Gly
385                 390                 395                 400

Leu Val Gln Pro Gly Gly Ser Leu Arg Leu Ser Cys Ala Ala Ser Gly
                405                 410                 415

Phe Thr Ile Ser Thr Asn Ala Met Ser Trp Val Arg Gln Ala Pro Gly
            420                 425                 430

Lys Gly Leu Glu Trp Ile Gly Val Ile Thr Gly Arg Asp Ile Thr Tyr
        435                 440                 445

Tyr Ala Ser Trp Ala Lys Gly Arg Phe Thr Ile Ser Arg Asp Asn Ser
    450                 455                 460

Lys Asn Thr Leu Tyr Leu Gln Met Asn Ser Leu Arg Ala Glu Asp Thr
465                 470                 475                 480

Ala Val Tyr Tyr Cys Ala Arg Asp Gly Gly Ser Ser Ala Ile Thr Ser
                485                 490                 495
```

```
Asn Asn Ile Trp Gly Gln Gly Thr Leu Val Thr Val Ser Ser Gly Gly
            500                 505                 510

Gly Gly Ser Gly Gly Gly Gly Ser Gln Ser Leu Val Glu Ser Gly Gly
        515                 520                 525

Gly Leu Val Gln Pro Gly Gly Ser Leu Arg Leu Ser Cys Ala Ala Ser
    530                 535                 540

Gly Phe Ser Phe Ser Ser Asn Tyr Trp Ile Cys Trp Val Arg Gln Ala
545                 550                 555                 560

Pro Gly Lys Gly Leu Glu Trp Ile Ala Cys Ile Tyr Val Gly Ser Ser
                565                 570                 575

Gly Asp Thr Tyr Tyr Ala Ser Ser Ala Lys Gly Arg Phe Thr Ile Ser
            580                 585                 590

Arg Asp Asn Ser Lys Asn Thr Leu Tyr Leu Gln Met Asn Ser Leu Arg
        595                 600                 605

Ala Glu Asp Thr Ala Val Tyr Tyr Cys Ala Arg Asp Ser Ser Ser Tyr
    610                 615                 620

Tyr Met Phe Asn Leu Trp Gly Gln Gly Thr Leu Val Thr Val Ser Ser
625                 630                 635                 640

Ala Ser Thr Lys Gly Pro Ser Val Phe Pro Leu Ala Pro Ser Ser Lys
                645                 650                 655

Ser Thr Ser Gly Gly Thr Ala Ala Leu Gly Cys Leu Val Lys Asp Tyr
            660                 665                 670

Phe Pro Glu Pro Val Thr Val Ser Trp Asn Ser Gly Ala Leu Thr Ser
        675                 680                 685

Gly Val His Thr Phe Pro Ala Val Leu Gln Ser Ser Gly Leu Tyr Ser
    690                 695                 700

Leu Ser Ser Val Val Thr Val Pro Ser Ser Ser Leu Gly Thr Gln Thr
705                 710                 715                 720

Tyr Ile Cys Asn Val Asn His Lys Pro Ser Asn Thr Lys Val Asp Lys
                725                 730                 735

Arg Val Glu Pro Lys Ser Cys Asp Lys Thr His Thr Cys Pro Pro Cys
            740                 745                 750

Pro Ala Pro Glu Ala Ala Gly Ala Pro Ser Val Phe Leu Phe Pro Pro
        755                 760                 765

Lys Pro Lys Asp Thr Leu Met Ile Ser Arg Thr Pro Glu Val Thr Cys
    770                 775                 780

Val Val Val Asp Val Ser His Glu Asp Pro Glu Val Lys Phe Asn Trp
785                 790                 795                 800

Tyr Val Asp Gly Val Glu Val His Asn Ala Lys Thr Lys Pro Arg Glu
                805                 810                 815

Glu Gln Tyr Asn Ser Thr Tyr Arg Val Val Ser Val Leu Thr Val Leu
            820                 825                 830

His Gln Asp Trp Leu Asn Gly Lys Glu Tyr Lys Cys Ala Val Ser Asn
        835                 840                 845

Lys Ala Leu Pro Ala Pro Ile Glu Lys Thr Ile Ser Lys Ala Lys Gly
    850                 855                 860

Gln Pro Arg Glu Pro Gln Val Tyr Thr Leu Pro Pro Ser Arg Asp Glu
865                 870                 875                 880

Leu Thr Lys Asn Gln Val Ser Leu Thr Cys Leu Val Lys Gly Phe Tyr
                885                 890                 895

Pro Ser Asp Ile Ala Val Glu Trp Glu Ser Asn Gly Gln Pro Glu Asn
            900                 905                 910
```

```
Asn Tyr Lys Thr Thr Pro Pro Val Leu Asp Ser Asp Gly Ser Phe Phe
        915                 920                 925

Leu Tyr Ser Lys Leu Thr Val Asp Lys Ser Arg Trp Gln Gln Gly Asn
    930                 935                 940

Val Phe Ser Cys Ser Val Met His Glu Ala Leu His Asn His Tyr Thr
945                 950                 955                 960

Gln Lys Ser Leu Ser Leu Ser Pro Gly Gly Gly Gly Gly Ser Gly Gly
                965                 970                 975

Gly Gly Ser Glu Val Gln Leu Leu Glu Ser Gly Gly Gly Leu Val Gln
            980                 985                 990

Pro Gly Gly Ser Leu Arg Leu Ser  Cys Ala Ala Ser Gly  Phe Ser Phe
        995                 1000                 1005

Ser Ser  Gly Tyr Asp Met Cys  Trp Val Arg Gln Ala  Pro Gly Lys
    1010                 1015                 1020

Gly Leu  Glu Trp Ile Ala Cys  Ile Ala Ala Gly Ser  Ala Gly Ile
    1025                 1030                 1035

Thr Tyr  Asp Ala Asn Trp Ala  Lys Gly Arg Phe Thr  Ile Ser Arg
    1040                 1045                 1050

Asp Asn  Ser Lys Asn Thr Leu  Tyr Leu Gln Met Asn  Ser Leu Arg
    1055                 1060                 1065

Ala Glu  Asp Thr Ala Val Tyr  Tyr Cys Ala Arg Ser  Ala Phe Ser
    1070                 1075                 1080

Phe Asp  Tyr Ala Met Asp Leu  Trp Gly Gln Gly Thr  Leu Val Thr
    1085                 1090                 1095

Val Ser  Ser Gly Gly Gly Gly  Ser Gly Gly Gly Gly  Ser Gly Gly
    1100                 1105                 1110

Gly Gly  Ser Gly Gly Gly Gly  Ser Asp Ile Gln Met  Thr Gln Ser
    1115                 1120                 1125

Pro Ser  Thr Leu Ser Ala Ser  Val Gly Asp Arg Val  Thr Ile Thr
    1130                 1135                 1140

Cys Gln  Ala Ser Gln Ser Ile  Ser Ser His Leu Asn  Trp Tyr Gln
    1145                 1150                 1155

Gln Lys  Pro Gly Lys Ala Pro  Lys Leu Leu Ile Tyr  Lys Ala Ser
    1160                 1165                 1170

Thr Leu  Ala Ser Gly Val Pro  Ser Arg Phe Ser Gly  Ser Gly Ser
    1175                 1180                 1185

Gly Thr  Glu Phe Thr Leu Thr  Ile Ser Ser Leu Gln  Pro Asp Asp
    1190                 1195                 1200

Phe Ala  Thr Tyr Tyr Cys Gln  Gln Gly Tyr Ser Trp  Gly Asn Val
    1205                 1210                 1215

Asp Asn  Val Phe Gly Gly Gly  Thr Lys Val Glu Ile  Lys
    1220                 1225                 1230
```

<210> SEQ ID NO 39
<211> LENGTH: 657
<212> TYPE: DNA
<213> ORGANISM: Artificial Sequence
<220> FEATURE:
<223> OTHER INFORMATION: synthesized

<400> SEQUENCE: 39

```
gcccttgtga tgacccagtc tccttccacc ctgtctgcat ctgtaggaga cagagtcacc     60

atcaattgcc aggccagtga ggacattgat acctatttag cctggtatca gcagaaacca    120

gggaaagccc ctaagctcct gatcttttat gcatccgatc tggcatctgg ggtcccatca    180
```

```
aggttcagcg gcagtggatc tgggacagaa ttcactctca ccatcagcag cctgcagcct    240

gatgattttg caacttatta ctgccaaggc ggttactata ctagtagtgc tgatacgagg    300

ggtgctttcg gcggagggac caaggtggag atcaaacgta cggtggctgc accatctgtc    360

ttcatcttcc cgccatctga tgagcagttg aaatctggaa ctgcctctgt tgtgtgcctg    420

ctgaataact tctatcccag agaggccaaa gtacagtgga aggtggataa cgccctccaa    480

tcgggtaact cccaggagag tgtcacagag caggacagca aggacagcac ctacagcctc    540

agcagcaccc tgacgctgag caaagcagac tacgagaaac acaaagtcta cgcctgcgaa    600

gtcacccatc agggcctgag ctcgcccgtc acaaagagct tcaacagggg agagtgt       657
```

```
<210> SEQ ID NO 40
<211> LENGTH: 219
<212> TYPE: PRT
<213> ORGANISM: Artificial Sequence
<220> FEATURE:
<223> OTHER INFORMATION: synthesized

<400> SEQUENCE: 40

Ala Leu Val Met Thr Gln Ser Pro Ser Thr Leu Ser Ala Ser Val Gly
1               5                   10                  15

Asp Arg Val Thr Ile Asn Cys Gln Ala Ser Glu Asp Ile Asp Thr Tyr
            20                  25                  30

Leu Ala Trp Tyr Gln Gln Lys Pro Gly Lys Ala Pro Lys Leu Leu Ile
        35                  40                  45

Phe Tyr Ala Ser Asp Leu Ala Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gly Gly Tyr Tyr Thr Ser Ser
                85                  90                  95

Ala Asp Thr Arg Gly Ala Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 41
<211> LENGTH: 5
<212> TYPE: PRT
<213> ORGANISM: Artificial Sequence
<220> FEATURE:
<223> OTHER INFORMATION: Synthesized
```

```
<400> SEQUENCE: 41

Gly Gly Gly Gly Ser
1               5
```